(12) United States Patent
Bosch Tubert et al.

(10) Patent No.: US 11,001,857 B2
(45) Date of Patent: *May 11, 2021

(54) GENE THERAPY COMPOSITION FOR USE IN DIABETES TREATMENT

(71) Applicant: UNIVERSITAT AUTÓNOMA DE BARCELONA, Barcelona (ES)

(72) Inventors: Fátima Bosch Tubert, Barcelona (ES); Eduard Ayuso López, Barcelona (ES); David Callejas Castiñeiras, Barcelona (ES)

(73) Assignee: UNIVERSITAT AUTONOMA DE BARCELONA, Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 14/951,810

(22) Filed: Nov. 25, 2015

(65) Prior Publication Data

US 2016/0074534 A1    Mar. 17, 2016

Related U.S. Application Data

(63) Continuation of application No. 13/809,777, filed as application No. PCT/EP2011/061847 on Jul. 12, 2011, now Pat. No. 9,309,534.

(30) Foreign Application Priority Data

Jul. 12, 2010  (ES) .................. 10169309.1

(51) Int. Cl.
| | | |
|---|---|---|
| *C12N 15/86* | (2006.01) | |
| *A61K 48/00* | (2006.01) | |
| *A61K 38/28* | (2006.01) | |
| *C07K 14/62* | (2006.01) | |
| *C12N 9/12* | (2006.01) | |
| *A61K 9/00* | (2006.01) | |

(52) U.S. Cl.
CPC ............ *C12N 15/86* (2013.01); *A61K 9/0019* (2013.01); *A61K 38/28* (2013.01); *A61K 48/005* (2013.01); *C07K 14/62* (2013.01); *C12N 9/1205* (2013.01); *C12Y 207/01002* (2013.01); *A61K 48/00* (2013.01); *C12N 2710/10041* (2013.01); *C12N 2750/14143* (2013.01); *C12N 2799/022* (2013.01); *C12N 2799/025* (2013.01); *C12N 2799/04* (2013.01)

(58) Field of Classification Search
None
See application file for complete search history.

(56) References Cited

U.S. PATENT DOCUMENTS

| | | |
|---|---|---|
| 5,139,941 A | 8/1992 | Muzyczka et al. |
| 5,436,146 A | 7/1995 | Shenk et al. |
| 5,446,143 A | 8/1995 | Simpson et al. |
| 5,464,758 A | 11/1995 | Gossen et al. |
| 5,478,745 A | 12/1995 | Samulski et al. |
| 5,741,683 A | 4/1998 | Zhou et al. |
| 6,001,650 A | 12/1999 | Colosi |
| 6,057,152 A | 5/2000 | Samulski et al. |
| 6,136,597 A | 10/2000 | Hope et al. |
| 6,156,303 A | 12/2000 | Russell et al. |
| 6,165,782 A | 12/2000 | Naldini et al. |
| 6,204,059 B1 | 3/2001 | Samulski et al. |
| 6,207,455 B1 | 3/2001 | Chang |
| 6,218,181 B1 | 4/2001 | Verma et al. |
| 6,268,213 B1 | 7/2001 | Samulski et al. |
| 6,277,633 B1 | 8/2001 | Olsen |
| 6,323,031 B1 | 11/2001 | Cichutek |
| 6,325,998 B1 | 12/2001 | Podsakoff et al. |
| 6,358,732 B1 | 3/2002 | Sedlacek et al. |
| 6,432,705 B1 | 8/2002 | Yee et al. |
| 6,491,907 B1 | 12/2002 | Rabinowitz et al. |
| 6,531,456 B1 | 3/2003 | Kurtzman et al. |
| 6,596,535 B1 | 7/2003 | Carter |
| 6,660,514 B1 | 12/2003 | Zolotukhin et al. |
| 6,951,753 B2 | 10/2005 | Shenk et al. |
| 7,056,502 B2 | 6/2006 | Hildinger et al. |
| 7,094,604 B2 | 8/2006 | Snyder et al. |
| 7,125,717 B2 | 10/2006 | Carter |
| 7,172,893 B2 | 2/2007 | Rabinowitz et al. |
| 7,198,951 B2 | 4/2007 | Gao et al. |
| 7,201,898 B2 | 4/2007 | Monahan et al. |
| 7,220,577 B2 | 5/2007 | Zolotukhin |
| 7,229,823 B2 | 6/2007 | Samulski et al. |
| 7,235,393 B2 | 6/2007 | Gao et al. |
| 7,250,406 B2 | 7/2007 | Tang et al. |
| 7,282,199 B2 | 10/2007 | Gao et al. |

(Continued)

FOREIGN PATENT DOCUMENTS

| | | |
|---|---|---|
| EP | 2394667 A1 | 12/2011 |
| EP | 2492347 A1 | 8/2012 |
| EP | 3101125 A1 | 12/2016 |
| WO | 1996040954 A1 | 12/1996 |
| WO | 1997049827 A2 | 12/1997 |

(Continued)

OTHER PUBLICATIONS

Dressman, D. AAV-Mediated Gene Transfer to Models of Muscular Dystrophy: Insights into Assembly of Multi-Subunit Membrane Proteins. 2001. University of Pittsburgh, Graduate Faculty of the School of Medicine, Department of Biochemistry and Molecular Genetics in partial fulfillment of the requirements for the degree of Doctor of Philosophy. 183 pages.*

(Continued)

*Primary Examiner* — Channing S Mahatan
(74) *Attorney, Agent, or Firm* — Sterne, Kessler, Goldstein & Fox P.L.L.C.

(57) ABSTRACT

New gene therapy constructions and compositions are the subject of present invention. The gene therapy compositions consist in adeno-associated vectors which jointly express insulin (Ins) and glucokinase (Gck) genes. The new gene therapy constructions are useful for treatment of diabetes either in dogs or human beings.

11 Claims, 17 Drawing Sheets

Figure 1:
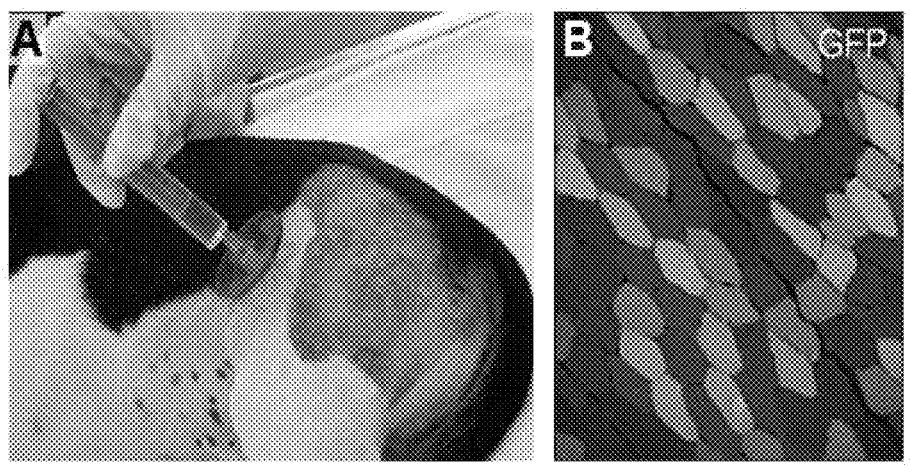
Figure 1:
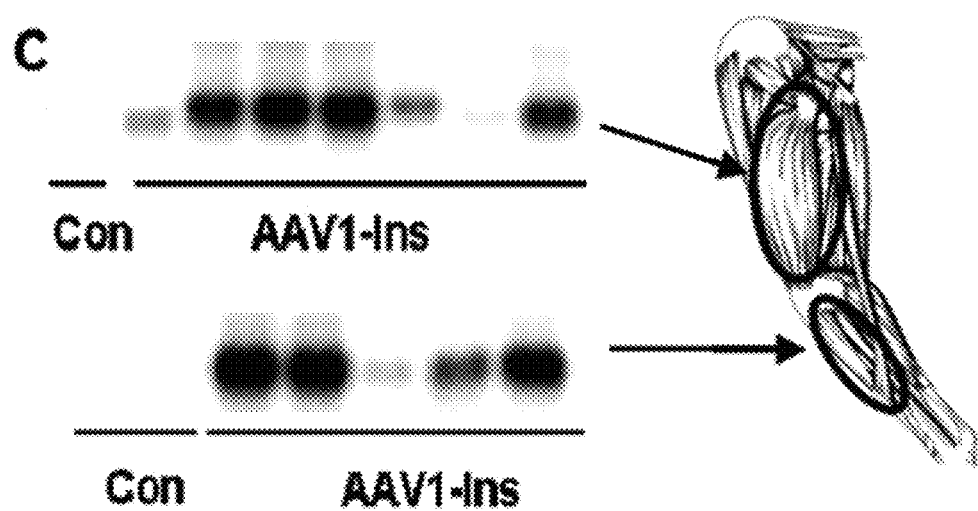

Specification includes a Sequence Listing.

(56) References Cited

U.S. PATENT DOCUMENTS

| | | | |
|---|---|---|---|
| 7,319,002 | B2 | 1/2008 | Wilson et al. |
| 7,425,443 | B2 | 9/2008 | Alam et al. |
| 7,439,065 | B2 | 10/2008 | Ferrari et al. |
| 7,456,683 | B2 | 11/2008 | Takano et al. |
| 7,790,449 | B2 | 9/2010 | Gao et al. |
| 8,865,881 | B2 | 10/2014 | Balazs et al. |
| 9,309,534 | B2 * | 4/2016 | Bosch Tubert ...... A61K 48/005 |
| 9,365,829 | B2 | 6/2016 | Simpson et al. |
| 9,732,329 | B2 | 8/2017 | Simpson et al. |
| 2002/0065239 | A1 | 5/2002 | Caplan et al. |
| 2003/0138772 | A1 | 7/2003 | Gao et al. |
| 2003/0148506 | A1 | 8/2003 | Kotin |
| 2003/0219409 | A1 | 11/2003 | Coffin et al. |
| 2004/0055023 | A1 | 7/2004 | Gao et al. |
| 2005/0187154 | A1 | 8/2005 | Kahn et al. |
| 2008/0075740 | A1 | 3/2008 | Gao et al. |
| 2010/0216709 | A1 | 8/2010 | Scheule et al. |
| 2010/0240029 | A1 | 9/2010 | Guarente et al. |
| 2011/0166210 | A1 | 7/2011 | Felber et al. |
| 2014/0344298 | A1 | 11/2014 | Bosch Tubert et al. |

FOREIGN PATENT DOCUMENTS

| | | |
|---|---|---|
| WO | 1998009524 A1 | 3/1998 |
| WO | 1998011244 A2 | 3/1998 |
| WO | 1998032869 A1 | 7/1998 |
| WO | 1999061601 A2 | 12/1999 |
| WO | 2000018899 A2 | 4/2000 |
| WO | 2000028004 A1 | 5/2000 |
| WO | 2000028061 A2 | 5/2000 |
| WO | 2010010887 A1 | 1/2001 |
| WO | 2001044481 A1 | 6/2001 |
| WO | 2001070276 A2 | 9/2001 |
| WO | 2001083692 A2 | 11/2001 |
| WO | 2001091803 A2 | 12/2001 |
| WO | 2001094605 A2 | 12/2001 |
| WO | 2002024234 A2 | 3/2002 |
| WO | 0249423 A1 | 6/2002 |
| WO | 2002049423 A1 | 6/2002 |
| WO | 2003014367 A1 | 2/2003 |
| WO | 2003052051 A2 | 6/2003 |
| WO | 2003052052 A2 | 6/2003 |
| WO | 2006001982 A2 | 1/2006 |
| WO | 2006110689 A2 | 10/2006 |
| WO | 2007000668 A2 | 1/2007 |
| WO | 2007058902 A1 | 5/2007 |
| WO | 2007127264 A2 | 11/2007 |
| WO | 2008027084 A2 | 3/2008 |
| WO | 2008061011 A2 | 5/2008 |
| WO | 2008071959 A1 | 6/2008 |
| WO | 2008103755 A1 | 8/2008 |
| WO | 2009120978 A2 | 10/2009 |
| WO | 2009151172 A1 | 12/2009 |
| WO | 2011004051 A1 | 1/2011 |
| WO | 2011127337 A2 | 10/2011 |
| WO | WO2011/154520 A1 | 12/2011 |
| WO | WO2015173308 A1 | 11/2015 |
| WO | WO2016193431 A1 | 12/2016 |
| WO | WO2018/060097 A1 | 4/2018 |

OTHER PUBLICATIONS

Parsons, G B et al.; "Ectopic expression of glucagon-like peptide 1 for gene therapy of type II diabetes," Gene Therapy, 2007, pp. 38-48, vol. 14.
International Search Report, dated Dec. 27, 2011, 4 pages.
Anderson HR, et al.; "Induction of alloxan/streptoztocin diabetes in dogs: a revised experimental technique," Lab Anim. 1993, pp. 281-285, vol. 27.
1997; Report of the Expert Committee on the Diagnosis and Classification of Diabetes Mellitus. Diabetes Care 20:1183-1197.
Eizirik, D.L., et al.; 2001. A choice of death—the signal-transduction of immune-mediated beta-cell apoptosis. Diabetologia 44:2115-2133.
Mathis, D., et al.; 2001. beta-Cell death during progression to diabetes. Nature 414:792-798.
Kahn, S.E., et al.; 2006. Mechanisms linking obesity to insulin resistance and type 2 diabetes. Nature 444:840-846.
Roglic, G., et al.; 2009. Mortality attributable to diabetes: estimates for the year 2010. Diabetes Res Clin Pract 87:15-19.
Soltez, et al; Diabetes in the Young: a Global Perspective; IDF Diabetes Atlas fourth edition; pp. 1-36.
Beran, D., et al.; 2006. Diabetes care in sub-Saharan Africa. Lancet 368:1689-1695.
Gale, E.A. 2006. Dying of diabetes. Lancet 368:1626-1628.
Greenwood, H.L., et al.; 2006. Regenerative medicine and the developing world. PLoS Med 3:e381, 1496-1500.
Heine, R.J., et al.; 1985. Mixing short and intermediate acting insulins in the syringe: effect on postprandial blood glucose concentrations in type I diabetics. Br Med J (Clin Res Ed) 290:1515-1516.
Binder, C., et al.; 1984. Insulin pharmacokinetics. Diabetes Care 7:188-199.
The Diabetes Control and Complications Trial Research Group. The effect of intensive treatment of diabetes on the development and progression of long-term complications in insulin-dependent diabetes mellitus.. 1993 N Engl J Med 329:977-986.
Cryer, P.E. 2001. Hypoglycemia risk reduction in type 1 diabetes. Exp Clin Endocrinol Diabetes 109 Suppl 2:S412-423.
Cryer, P.E. 2002. Hypoglycaemia: the limiting factor in the glycaemic management of Type I and Type II diabetes. Diabetologia 45:937-948.
Correa-Giannella, M.L., et al.; 2009. Pancreatic islet transplantation. Diabetol Metab Syndr 1:9; pp. 1-7.
Shapiro, A.M., et al.; 2000. Islet transplantation in seven patients with type 1 diabetes mellitus using a glucocorticoid-free immunosuppressive regimen. N Engl J Med 343:230-238.
Ryan, E.A., et al.; 2005. Five-year follow-up after clinical islet transplantation. Diabetes 54:2060-2069.
Elliott, R.B., et al; 2007. Live encapsulated porcine islets from a type 1 diabetic patient 9.5 yr after xenotransplantation. Xenotransplantation 14:157-161.
Hering, B.J., et al.; 2009. Pig-to-nonhuman primate islet xenotransplantation. Transpl Immunol 21:81-86.
Trucco, M. 2005. Regeneration of the pancreatic beta cell. J Clin Invest 115:5-12.
Dong, H., et al.; 2001. Hepatic insulin production for type 1 diabetes. Trends Endocrinol Metab 12:441-446.
Lee, H.C., et al.; 2000. Remission in models of type 1 diabetes by gene therapy using a single-chain insulin analogue. Nature 408:483-488.
Cheung, A.T., et al.; 2000. Glucose-dependent insulin release from genetically engineered K cells. Science 290:1959-1962.
Ferber, S., et al.; 2000. Pancreatic and duodenal homeobox gene 1 induces expression of insulin genes in liver and ameliorates streptozotocin-induced hyperglycemia. Nat Med 6:568-572.
Kojima, H., et al.; 2003. NeuroD-betacellulin gene therapy induces islet neogenesis in the liver and reverses diabetes in mice. Nat Med 9:596-603. Epub 2003 Apr. 2021.
Kahn, B.B. 1996. Lilly lecture 1995. Glucose transport: pivotal step in insulin action. Diabetes 45:1644-1654.
Printz, R.L., et al.; 1993. Mammalian glucokinase. Annu Rev Nutr 13:463-496.
Postic, C., et al.; 1994. Development and regulation of glucose transporter and hexokinase expression in rat. Am J Physiol 266:E548-559.
Printz, R.L., et al.; 1993. Hexokinase II mRNA and gene structure, regulation by insulin, and evolution. J Biol Chem 268:5209-5219.
Riu E. et al.; 2002. Counteraction of type 1 diabetic alterations by engineering skeletal muscle to produce insulin: insights from transgenic mice. Diabetes 51:704-711.
White, M.F. et al.; 1994. The insulin signaling system. J Biol Chem 269:1-4.

(56) References Cited

OTHER PUBLICATIONS

Otaegui, P.J., et al.; 2000. Expression of glucokinase in skeletal muscle: a new approach to counteract diabetic hyperglycemia. Hum Gene Ther 11:1543-1552.
Matschinsky, F.M. 1996. Banting Lecture 1995. A lesson in metabolic regulation inspired by the glucokinase glucose sensor paradigm. Diabetes 45:223-241.
Jimenez-Chillaron, J.C., et al.; 1999. Increased glucose disposal induced by adenovirus-mediated transfer of glucokinase to skeletal muscle in vivo. Faseb J 13:2153-2160.
Otaegui, P.J., et al.; 2002. Glucose-regulated glucose uptake by transplanted muscle cells expressing glucokinase counteracts diabetic hyperglycemia. Hum Gene Ther 13:2125-2133.
Mas, A., et al.; 2006. Reversal of type 1 diabetes by engineering a glucose sensor in skeletal muscle. Diabetes 55:1546-1553.
Daya S et al.; 2008. Gene therapy using adeno-associated virus vectors. Clin Microbiol Rev 21(4):583-593.
Brantly ML, et al.; 2009. Sustained transgene expression despite T lymphocyte responses in a clinical trial of rAAV1-AAT gene therapy Proc Natl Acad Sci U S A 106(38):16363-16368.
Kaplitt MG, et al.; 2007. Safety and tolerability of gene therapy with an adeno-associated virus (AAV) borne GAD gene for Parkinson's disease: an open label, phase I trial.Lancet 369(9579):2097-2105.
Maguire AM,et al.; 2009. Age-dependent effects of RPE65 gene therapy for Leber's congenital amaurosis: a phase 1 dose-escalation trial. Lancet 374(9701):1597-1605.
Maguire AM, et al.; 2008. Safety and efficacy of gene transfer for Leber's congenital amaurosis.N Engl J Med 358(21):2240-2248.
Manno CS, et al.; 2006. Successful transduction of liver in hemophilia by AAV-Factor IX and limitations imposed by the host immune response. Nat Med 12(3):342-347.
Mendell Jr, et al.; 2009. Limb-girdle muscular dystrophy type 2D gene therapy restores alpha-sarcoglycan and associated proteins. Ann Neurol 66(3):290-297.
Stroes ES, et al.; 2008. Intramuscular administration of AAV1-lipoprotein lipase S447X lowers triglycerides in lipoprotein lipase-deficient patients. Arterioscler Thromb Vasc Biol 28(12):2303-2304.
Jiang H, et al.; 2006. Evidence of multiyear factor IX expression by AAV-mediated gene transfer to skeletal muscle in an individual with severe hemophilia B. Mol Ther 14(3):452-455.
Niemeyer GP, et al.; 2009. Long-term correction of inhibitor-prone hemophilia B dogs treated with liver-directed AAV2-mediated factor IX gene therapy. Blood 113(4):797-806.
Simonelli F, et al.; 2010. Gene therapy for Leber's congenital amaurosis is safe and effective through 1.5 years after vector administration. Mol Ther 18(3):643-650.
Sharp, P.M. et al.; 1987. The codon Adaptation Index—a measure of directional synonymous codon usage bias, and its potential applications. Nucleic Acids Res. 15 (3), 1281-1295.
Ayuso E, et al.; 2010. High AAV vector purity results in serotype- and tissue-independent enhancement of transduction efficiency. Gene Ther. 17(4):503-10.
Oh Tae Keun, et al.; "Gene therapy for diabetes mellitus in rats by intramuscular injection of lentivirus containing insulin gene," Diabetes Research and Clinical Practice, 2006, pp. 233-240, vol. 71.
Callejas, D., et al., "Treatment of Diabetes and Long-Term Survival After Insulin and Glucokinase Gene Therapy," Diabetes, vol. 62, pp. 1718-1729 (May 2013).
Jaen, Maria Luisa, et al., "Long-Term Efficacy and Safety of Insulin and Glucokinase Gene Therapy for Diabetes: 8-Year Follow-Up in Dogs," Molecular Therapy Methods & Clinical Development, vol. 6, pp. 1-7, Published Online Jun. 1, 2017.
Clinical Biochemisry of Domestic Animals, 6th Edition, "Chapter 3—Carbohydrate Metabolism and Its Diseases," Editors, Jiro Jerry Kaneko, John W. Harvey, Michael L. Bruss, pp. 45-80 (2008).
Mann, C., et al., "Gene Therapy for Type I Diabetes by Engineering Skeletal Muscle to Express Insulin and Glucokinase (GK): Pre-Clinical Studies in Diabetic Dogs," Abstract No. 420-P (2008).

O'Brien, Timothy, "Gene Therapy for Type 1 Diabetes Moves a Step Closer to Reality," Diabetes, vol. 62, pp. 1396-1397 (May 2013).
"Definition and Diagnosis of Diabetes Mellitus and Intermediate Hyperglycemia," Report of a WHO/IDF Consultation, World Health Organization 2006.
Allera-Moreau, C., Delluc-Clavières, A., Castano, C., Van den Berghe, L., Golzio, M., Moreau, M., Teissié, J., Arnal, J. F. and Prats, A.C., 2007. Long term expression of bicistronic vector driven by the FGF-1 IRES in mouse muscle. BMC biotechnology, 7(1), p. 74.
Liu et al, Hydrodynamics-based transfection in animals by systemic administration of plasmid DNA. Gene Ther. vol. 6, pp. 1258-1266, 1999.
Loiler et al, Localized gene expression following administration of adeno-associated viral vectors via pancreatic ducts. Mol. Ther. vol. 12, pp. 519-527, 2005.
Lomb DJ, et al, Sirtuins regulate key aspects of lipid metabolism. Biochim Biophys Acta vol. 1804(8), pp. 1652-1657,2010.
Xiao et al, Gene therapy vectors based on adeno-associated virus type 1. J. Virology vol. 73:3994, 1999.
Lu et al, Pancreatic-specific inactivation of IGF-I gene causes enlarged pancreatic islets and significant resistance to diabetes. Diabetes vol. 53, pp. 3131-3141, 2004.
Mahendroo M, et al., Tissue-specific and Hormonally Controlled Alternative Promoters Regulate Aromatase Cytochrome P450 Gene Expression in Human Adipose Tissue. J. Biol. Chem. vol. 268, pp. 19463-19470, 1993.
Monica George et al, [beta] cell expression of Igf-I leads to recovery from type 1 diabetes. Journal of Clinical Investigation vol. 109 (9), pp. 1153-1163, May 2002.
Munoz S, et al., Chronically increased glucose uptake by adipose tissue leads to lactate production and improved Insulin sensitivity rather than obesity in the mouse. Diabetologia vol. 53(11), pp. 2417-2430, 2010.
Orellana-Gavalda et al., Molecular therapy for obesity and diabetes based on a long-term increase in hepatic fatty-acid oxidation, Hepatology, 2011, vol. 53(3), pp. 821-32, Dec. 10, 2010.
Otaegui et al, Prevention of obesity and insulin resistance by glucokinase expression in skeletal muscle of transgenic mice. The FASEB Journal express article. Online 10.1096/fj.03-0081fje,18. 09.2003.
Rabinowitz J et al, Cross-Packaging of a Single Adeno-Associated Virus (AAV) Type 2 Vector Genome into Multiple AAV Serotypes Enables Transduction with Broad Specificity, vol. 76(2), pp. 791-801, Jan. 2002.
Rui et al, Counteraction of Type 1 Diabetic Alterations by Engineering Skeletal Muscle to Produce Insulin Insights fron Transgenic Mice, Diabetes vol. 51 pp. 704-711, Mar. 2002.
Sarruf et al. Fibroblast Growth Factor 21 Action in the Brain Increases Energy Expenditure and Insulin Sensitivity in obese Rats. Diabetes 2010; 59:1817-1824, Apr. 27, 2010.
Sherry et al, Teplizumab for treatment of type 1 diabetes (Protege study): 1-year results from a randomised, placebo-controlled trial. Lancet vol. 378, pp. 487-497, 2011.
Srivastava et al, Nucleotide sequence and organization of the adeno-associated virus 2 genome J. Vir. vol. 45(2), pp. 555-64, 1983.
Spiegelman B, et al., Regulation Expression Syndromes of Adipocyte Gene in Differentiation and of Obesity/Diabetes. J. Biol. Chem. vol. 268(10), pp. 6823-6826, 1993.
Wang et al, Improved neuronal transgene expression from an AAV-2 vector with a hybrid CMV enhancer/PDGF-βpromoter, J Gene Med., vol. 7, pp. 945-955, Mar. 9, 2005.
Anguela, X.M., et al., "Nonviral-Mediated Hepatic Expression of IGF-I Increases Treg Levels and Suppresses Autoimmune Diabetes in Mice," Diabetes, 62(2): 551-560, The American Diabetes Association, United States (2013).
Ayuso, E., and Bosch, F., "Highlights on AAV Mediated Gene Transfer: Introduction," in *The Clinibook: Clinical Gene Transfer State of the Art*, Cohen-Haguenauer, O., ed., pp. 31-34, Éditions EDK, Paris (2012).

(56) References Cited

OTHER PUBLICATIONS

Ayuso, E., et al., "AAV Gene Therapy for Diabetes Mellitus," in *The Clinibook: Clinical Gene Transfer State of the Art*, Cohen-Haguenauer, O., ed., pp. 62-70, Éditions EDK, Paris (2012).

Ayuso, E., et al., "Reference Materials For The Characterization of Adeno-Associated Viral Vectors," in *The Clinibook: Clinical Gene Transfer State of the Art*, Cohen-Haguenauer, O., ed., pp. 83-90, Éditions EDK, Paris (2012).

Ayuso, E., et al., "Production, Purification and Characterization of Adeno-Associated Vectors," *Current Gene Therapy*, 10(6): 423-426, Bentham Science Publishers Ltd., Netherlands (2010).

Fagoe, ND., "A compact dual promoter adeno-associated viral vector for efficient delivery of two genes to dorsal root ganglion neurons," *Gene Therapy*, 21: 242-252, Macmillan Publishers Limited, United States (2014).

Garcia, M., et al., "Phosphofructo-1-Kinase Deficiency Leads to a Severe Cardiac and Hematological Disorder in Addition to Skeletal Muscle Glycogenosis," *PLoS Genetics*, 5(8): e1000615, pp. 1-12, Public Library of Science, United States (2009).

Haurigot, V., et al., "Future Directions: Gene Therapy for Diabetes," Part 13, Ch. 70, in Textbook of *Diabetes*, 5th Edition, Holt, R., et al., eds., pp. 1029-1037, Wiley-Blackwell, United States (2017).

Jaén, ML., et al., "Long-Term Efficacy and Safety of Insulin and Glucokinase Gene Therapy for Diabetes: 8-Year Follow-Up in Dogs," *Molecular Therapy-Methods Clinical Development*, 6:1-7, Elsevier, Netherlands (2017).

Mann, C.J., et al., "Skeletal Muscle Metabolism in the Pathology and Treatment of Type 1 Diabetes," *Current Pharmaceutical Design*, 16(8): 1002-1020, Bentham Science Publishers Ltd., Netherlands (2010).

Mann, C.J., et al., "Molecular Signature of the Immune and Tissue Response to Non-Coding Plasmid DNA in Skeletal Muscle After Electrotransfer," *Gene Therapy*19(12):1177-1186, Macmillan Publishers Limited, United States (2012).

Otaegui, P., et al., "Expression of Glucokinase in Skeletal Muscle: A New Approach to Counteract Diabetic Hyperglycemia," *Human Gene Therapy*, 11: 1543-1552, Mary Ann Liebert, Inc., United States (2000).

Riu, E., et al., "Counteraction of Type 1 Diabetic Alterations by Engineering Skeletal Muscle to Produce Insulin. Insights From Transgenic Mice," *Diabetes*, 51: 704-711, American Diabetes Association (2002).

Monahan P. et al, AAV vectors: is clinical success on the horizon?, Gene Therapy, vol. 7, pp. 24-30, Jan. 17, 2000.

Agudo, J. et al, IGF-I mediates regeneration of endocrine pancreas by increasing beta cell replication through cell cycle protein modulation in mice. Diabetologia vol. 51, pp. 1862-1872, 2008.

Ahi et al, Adenoviral Vector Immunity: Its implications and circumvention strategies. Curr. Gene Ther. vol. 11(4), pp. 307-320, Aug. 2011.

Cohen HY. et al,Calorie restriction promotes mammalian cell survival by inducing the SIRT1 deacetylase. Science vol. 305, pp. 390-392, 2004.

Al-Dossari Mohammad et al, Evaluation of viral and mammalian promoters for driving transgene expression in mouse liver. Biochemical and Biophysical Research Communications vol. 339(2), pp. 673-678, Jan. 13, 2006.

Alexopoulou et al, The CMV earlyenhancer/chicken beta actin (CAG) promoter can be used to drive transgene expressionduring the differentiation of murine embryonic stem cells into vascular progenitors. BMC Cell Biol. vol. 9(2), pp. 1-11 2008.

D. A. Sarruf et al., Fibroblast growth factor 21 action in the brain increases energy expenditure and insulin sensitivity in obese rats. Diabetes. vol. 59(7), pp. 1817-1824, 2010.

Deng XQ,. et al, The expression of SIRT1 in nonalcoholic fatty liver disease induced by high-fat diet rats. Liver Int vol. 27, pp. 708-715, 2007.

Amado and Chen, Lentiviral Vectors—the Promise of Gene Therapy Within Reach?, Science vol. 285, pp. 574-6 ,1999.

American Diabetes Association, Diagnosis and Classification of Diabetes Mellitus, Diabetes Care, vol. 33, Suppl. S62-69, 2010.

Doege H. et al., Silencing of hepatic fatty acid transporter protein 5 in vivo reverses diet-induced non-alcoholic fatty liver disease and improves hyperglycemia, J Biol Chem, 2008, vol. 283(32), pp. 22186-92, Jun. 3, 2008.

Apparailly et al, Adeno-associated virus pseudotype 5 vector improves gene transfer in arthritic joints., Hum Gene Ther., vol.16(4):426-34, May 4, 2005.

Ayuso E, et al, Production, purification and characterization of adeno-associated vectors, Curr. Gene Ther., vol. 10, pp. 423-436, Dec. 1, 2010.

Erion, D., et al, SirT1 Knockdown in Liver Decreases Basal Hepatic Glucose Production and Increases Hepatic Insulin Responsiveness in Diabetic Rats, PNAS, vol. 106(27), pp. 11288-11293, Jul. 7, 2009.

Banks et al. Sirt1 gain of function increases energy efficiency and prevents diabetes in mice. Cell Metab. 8(4), pp. 333-41, 2008.

Franckhauser S, et al., Increased Fatty Acid Re-esterification by PEPCK Overexpression in Adipose Tissue Leads to ObesityWithout Insulin Resistance. Diabetes vol. 51, pp. 624-630, 2002.

George et al, Beta cell expression of IGF-I leads to recovery from type 1 diabetes. J. Clin. Invest. vol. 109, pp. 1153-1163, 2002.

Bergerot et al, Effects of insulin like growth factor-1 and insulin on effector T cells generating autoimmune diabetes. Diabetes Metab. vol. 22, pp. 235-239, 1996.

Bergerot et al, Insulin-like growth factor-1 (IGF-1) protects NOD mice from insulitis and diabetes. Clin. Exp. Immunol. vol. 102, pp. 335-340, 1995.

Berglund et al, Fibroblast Growth Factor 21 Controls Glycemia via Regulation of Hepatic Glucose Flux and Insulin Sensitivity, Endocrinology, vol. 150, pp. 4084-4093, May 21, 2009.

Goudy K, et al.,Inducible Adeno-Associated Virus-Mediated IL-2 Gene Therapy Prevents Autoimmune Diabetes. J. Immunol. vol. 186(6), pp. 3779-3786, 2011.

Graves R, et al., Analysis of a tissue-specific enhancer: ARF6 regulates adipogenic gene expression. Mol. Cell Biol. vol. 12(3), pp. 1202-1208, 1992.

Graves RA et al, Identification of a potent adipocyte-specific enhancer: involvement of an NF-1-like factor. Genes & Development vol. 5(3), pp. 428-437, Jan. 3, 1991.

Gros et al, Insulin Production by Engineered Muscle Cells. Human Gene Therapy vol. 10, pp. 1207-1217, Jan. 5, 1999.

Bordone et al, SIRT1 transgenic mice show phenotypes resembling calorie restriction. Aging Cell. vol. 6(6), pp. 759-67, 2007.

Bordone, L., et al, Sirt1 Regulates Insulin Secretion by Repressing UCP2 in Pancreatic βCells. PLOS Biology, vol. 4(2), e31, pp. 210-220 (Feb. 2006-published online Dec. 27, 2005), Feb. 2006.

Gros et al, Regulated Production of Mature Insulin by Non-β-cells. Human Gene Therapy vol. 8, pp. 2249-2259, Oct. 12, 1997.

Hafenrichter et al, Quantitative evaluation of liver-specific promoters from retroviral vectors after in vivo transduction of hepatocytes. Blood vol. 84, pp. 3394-3404, 1994.

Boulos et al, Assessment of CMV, RSV and SYN1 promoters and the woodchuck post-transcriptional regulatory element in adenovirus vectors for transgene expression in cortical neuronal cultures. Brain Research vol. 1102, pp. 27-38, 2006.

Boyer B, et al., The Mitochondrial Uncoupling Protein Gene in Brown Fat:Correlation between DNaseI Hypersensitivity and Expression in Transgenic Mice. Mol. Cell Biol. vol. 11, pp. 4147-4156, 1991.

Henikoff and Henikoff, Amino acid substitution matrices from protein blocks. Comparison matrix: Blossum. Proc. Natl. Acad. Sci. USA. vol. 89, pp. 10915-10919, 1992.

Hondares E. et al, Hepatic FGF21 Expression Is Induced at Birth via PPARa in Response to Milk Intake and contributes to Thermogenic Activation of Neonatal Brown Fat, Cell Metab., vol. 11, pp. 206-212, Mar. 3, 2011.

Kaino et al, Insulin-like growth factor I (IGF-I) delays the onset of diabetes in non-obese diabetic (NOD) mice. Diabetes Res. Clin. Pract. vol. 34, pp. 7-11, 1996.

(56) References Cited

OTHER PUBLICATIONS

Callejas et al, Gene Therapy for Type I Diabetes by Engineering Skeletal Muscle to Express Insulin and Glucokinase (GK): Preclinical studies in Diabetic Dogs. Poster presentation, 2007.

Callejas et al, Gene Therapy for Type I Diabetes by Engineering Skeletal Muscle to Express Insulin and Glucokinase (GK): Preclinical studies in Diabetic Dogs. Poster presentation, 2008.

Cao D, Adipose tissue angiogenesis as a therapeutic target for obesity and metabolic diseases. Nature Rev. vol. 9, pp. 107-115, 2010.

Kamata et al., Structural Basis for Allosteric Regulation of the Monomeric Allosteric Enzyme Human Glucokinase. Structure vol. 12, pp. 429-438, Mar. 2004.

Kapturczak et al., Transduction of Human and Mouse Pancreatic Islet Cells Using a Bicistronic Recombinant Adeno-associated Viral Vector. Molecular Therapy vol. 5(2), pp. 154-160, 02.2002.

Keck P, et al.,Vascular permeability factor, an endothelial cell mitogen related to PDGF. Science vol. 246, pp. 1309-1312, 1989.

Kharitonenkov et al., FGF-21 as a novel metabolic regulator, Journal of Clinical Investigation, vol. 115, No. 6, pp. 1627-1635, Jun. 1, 2005.

Kim et al, Genebank NP_001104746.1, insulin-like growth factor 1 isoform 5 preproprotein [Mus musculus], Dec. 2007.

Kulkarni et al, beta-cell-specific deletion of the Igf1 receptor leads to hyperinsulinemia and glucose intolerance but does not alter beta-cell mass. Nat. Genet. vol. 31, pp. 111-115, 2002.

Ceddia RB, Direct metabolic regulation in skeletal muscle and fat tissue by leptin: implications for glucose and fatty acids homeostasis. Int J Obes (Lund), vol. 29(10), pp. 1175-1183, 2005.

Chao et al, Several log increase in therapeutic transgene delivery by distinct adeno-associated viral serotype vectors. Molecular Therapy vol. 2(6):619-623, 2000.

Chao L. et al, Adipose tissue is required for the antidiabetic, but not for the hypolipidemic, effect of thiazolidinediones, J . Clin. Invest., vol. 106, pp. 1221-1228, Nov. 15, 2000.

Cheetham et al, The effects of repeated daily recombinant human insulin-like growth factor I administration in adolescents with type 1 diabetes. Diabet. Med. vol. 12, pp. 885-892, 1995.

Lagos-Quintana et al, Identification of Tissue-Specific MicroRNAs from Mouse. Current Biology vol. 12, pp. 735-739, Apr. 2002.

Larose M, et al., Essential cis-Acting Elements in Rat Uncoupling Protein Gene Are in an Enhancer Containing a Complex Retinoic Acid Response Domain. J. Biol. Chem. 1996; 271(49):31533-31542, 1996.

Chen et al., TiProD: the Tissue-specific Promoter Database, Nucleic Acids Research, 2006, J4:D104-D107, 2006.

Li et al, A small regulatory element from chromosome 19 enhances liver-specific gene expression. Gene Therapy 16, pp. 43-51, 2009.

* cited by examiner mhINS mhGK

A

B

SEQUENCE LISTING

<160> NUMBER OF SEQ ID NOS: 8

<210> SEQ ID NO 1
<211> LENGTH: 2165
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1308)..(1640)

<400> SEQUENCE: 1

```
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120 actagggggtt ccttgtagtt aatgattaac ccgccatgct acttatctac gtagccatgc    180
tctagacatg gctcgacaga tctcaatatt ggccattagc catattattc attggttata    240
tagcataaat caatattggc tattggccat tgcatacgtt gtatctatat cataatatgt    300
acatttatat tggctcatgt ccaatatgac cgccatgttg gcattgatta ttgactagtt    360
attaatagta atcaattacg gggtcattag ttcatagccc atatatggag ttccgcgtta    420
```

```
cataacttac ggtaaatggc ccgcctggct gaccgcccaa cgaccccgc ccattgacgt      480 caataatgac gtatgttccc atagtaacgc caatagggac tttccattga cgtcaatggg      540
tggagtattt acggtaaact gcccacttgg cagtacatca agtgtatcat atgccaagtc      600 cgcccccttat tgacgtcaat gacggtaaat ggcccgcctg gcattatgcc cagtacatga     660
ccttacggga ctttcctact tggcagtaca tctacgtatt agtcatcgct attaccatgg      720
tgatgcggtt ttggcagtac accaatgggc gtggatagcg gtttgactca cggggatttc      780
caagtctcca ccccattgac gtcaatggga gtttgttttg gcaccaaaat caacgggact      840
ttccaaaatg tcgtaacaac tgcgatcgcc cgccccgttg acgcaaatgg gcggtaggcg      900
tgtacggtgg gaggtctata taagcagagc tcgtttagtg aaccgtcaga tcactagaag      960
ctttattgcg gtagtttatc acagttaaat tgctaacgca gtcagtgctt ctgacacaac     1020
agtctcgaac ttaagctgca gtgactctct taaggtagcc ttgcagaagt tggtcgtgag     1080
gcactgggca ggtaagtatc aaggttacaa gacaggttta aggagaccaa tagaaactgg     1140
gcttgtcgag acagagaaga ctcttgcgtt tctgataggc acctattggt cttactgaca     1200
tccactttgc ctttctctcc acaggtgtcc actcccagtt caattacagc tcttaaggct     1260
agagtactta atacgactca ctataggcta gcctcgagaa ttctgcc atg gcc ctg       1316
                                                     Met Ala Leu
                                                      1 tgg atg cgc ctc ctg ccc ctg ctg gcg ctg ctg gcc ctc tgg gga cct       1364
Trp Met Arg Leu Leu Pro Leu Leu Ala Leu Leu Ala Leu Trp Gly Pro
 5              10                  15 gac cca gcc gca gcc ttt gtg aac caa cac ctg tgc ggc tca gat ctg       1412
Asp Pro Ala Ala Ala Phe Val Asn Gln His Leu Cys Gly Ser Asp Leu
 20              25                  30                  35 gtg gaa gct ctc tac cta gtg tgc ggg gaa cga ggc ttc ttc tac aca       1460
Val Glu Ala Leu Tyr Leu Val Cys Gly Glu Arg Gly Phe Phe Tyr Thr
                 40                  45                  50 ccc agg acc aag cgg gag gca gag gac ctg cag gtg ggg cag gtg gag       1508
Pro Arg Thr Lys Arg Glu Ala Glu Asp Leu Gln Val Gly Gln Val Glu
             55                  60                  65 ctg ggc ggg ggc cct ggt gca ggc agc ctg cag ccc ttg gcc ctg gag       1556
Leu Gly Gly Gly Pro Gly Ala Gly Ser Leu Gln Pro Leu Ala Leu Glu
         70                  75                  80 ggg tcg cga cag aag cgt ggc att gtg gaa caa tgc tgt acc agc atc       1604
Gly Ser Arg Gln Lys Arg Gly Ile Val Glu Gln Cys Cys Thr Ser Ile
     85                  90                  95 tgc tcc ctc tac cag ctg gag aac tac tgc aac tag acgcagctgc           1650
Cys Ser Leu Tyr Gln Leu Glu Asn Tyr Cys Asn
100                 105                 110 aagcttatcg ataccgtcga cctcgaggaa ttcacgcgtg gtacctctag agtcgacccg     1710
ggcggccgct tccctttagt gagggttaat gcttcgagca gacatgataa gatacattga     1770
tgagtttgga caaaccacaa ctagaatgca gtgaaaaaaa tgctttattt gtgaaatttg     1830
tgatgctatt gctttatttg taaccattat aagctgcaat aaacaagtta acaacaacaa     1890
ttgcattcat tttatgtttc aggttcaggg ggagatgtgg gaggtttttt aaagcaagta     1950
aaacctctac aaatgtggta aaatccgata agggactaga gcatggctac gtagataagt     2010
agcatggcgg gttaatcatt aactacaagg aaccccctagt gatggagttg gccactccct     2070
ctctgcgcgc tcgctcgctc actgaggccg ggcgaccaaa ggtcgcccga cgcccgggct     2130 tgcccgggc ggcctcagtg agcgagcgag cgcgc                                2165
```

```
<210> SEQ ID NO 2
<211> LENGTH: 110
<212> TYPE: PRT
<213> ORGANISM: Artificial Sequence
<220> FEATURE:
<223> OTHER INFORMATION: Synthetic Construct

<400> SEQUENCE: 2

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser Asp Leu Val Glu Ala Leu Tyr Leu Val Cys Gly Glu Arg Gly Phe
        35                  40                  45

Phe Tyr Thr Pro Arg Thr Lys Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Arg Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 3
<211> LENGTH: 4132
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1397)..(2794)

<400> SEQUENCE: 3
```

| | | | | | |
|---|---|---|---|---|---|
| gcagctgcgc | gctcgctcgc | tcactgaggc | cgcccgggca | aagcccgggc gtcgggcgac | 60 |
| ctttggtcgc | ccggcctcag | tgagcgagcg | agcgcgcaga | gagggagtgg ccaactccat | 120 |
| cactagggt | tccttgtagt | taatgattaa | cccgccatgc | tacttatcta cgtagccatg | 180 |
| ctctagacat | ggctcgacag | atctcaatat | tggccattag | ccatattatt cattggttat | 240 |
| atagcataaa | tcaatattgg | ctattggcca | ttgcatacgt | tgtatctata tcataatatg | 300 |
| tacatttata | ttggctcatg | tccaatatga | ccgccatgtt | ggcattgatt attgactagt | 360 |
| tattaatagt | aatcaattac | ggggtcatta | gttcatagcc | catatatgga gttccgcgtt | 420 |
| acataactta | cggtaaatgg | cccgcctggc | tgaccgccca | acgacccccg cccattgacg | 480 |
| tcaataatga | cgtatgttcc | catagtaacg | ccaatagga | ctttccattg acgtcaatgg | 540 |
| gtggagtatt | tacggtaaac | tgcccacttg | gcagtacatc | aagtgtatca tatgccaagt | 600 |
| ccgcccccta | ttgacgtcaa | tgacggtaaa | tggcccgcct | ggcattatgc ccagtacatg | 660 |
| accttacggg | actttcctac | ttggcagtac | atctacgtat | tagtcatcgc tattaccatg | 720 |
| gtgatgcggt | tttggcagta | caccaatggg | cgtggatagc | ggtttgactc acggggattt | 780 |
| ccaagtctcc | accccattga | cgtcaatggg | agtttgtttt | ggcaccaaaa tcaacgggac | 840 |
| tttccaaaat | gtcgtaacaa | ctgcgatcgc | cgcccccgtt | gacgcaaatg ggcggtaggc | 900 |
| gtgtacggtg | ggaggtctat | ataagcagag | ctcgtttagt | gaaccgtcag atcactagaa | 960 |
| gctttattgc | ggtagtttat | cacagttaaa | ttgctaacgc | agtcagtgct tctgacacaa | 1020 |
| cagtctcgaa | cttaagctgc | agtgactctc | ttaaggtagc | cttgcagaag ttggtcgtga | 1080 |

```
ggcactgggc aggtaagtat caaggttaca agacaggttt aaggagacca atagaaactg      1140
ggcttgtcga gacagagaag actcttgcgt ttctgatagg cacctattgg tcttactgac      1200
atccactttg cctttctctc cacaggtgtc cactcccagt tcaattacag ctcttaaggc      1260
tagagtactt aatacgactc actataggct agcctcgaga attccctcag ccagacagtc      1320
cttacctgca acaggtggcc tcaggagtca ggaacatctc tacttcccca acgacccctg      1380
ggttgtcctc tcagag atg gct atg gat act aca agg tgt gga gcc cag ttg      1432
              Met Ala Met Asp Thr Thr Arg Cys Gly Ala Gln Leu
              1               5                   10 ttg act ctg gtc gag cag atc ctg gca gag ttc cag ctg cag gag gaa         1480
Leu Thr Leu Val Glu Gln Ile Leu Ala Glu Phe Gln Leu Gln Glu Glu
        15                  20                  25 gac ctg aag aag gtg atg agc cgg atg cag aag gag atg gac cgt ggc         1528
Asp Leu Lys Lys Val Met Ser Arg Met Gln Lys Glu Met Asp Arg Gly
30                  35                  40 ctg agg ctg gag acc cac gag gag gcc agt gta aag atg tta ccc acc         1576
Leu Arg Leu Glu Thr His Glu Glu Ala Ser Val Lys Met Leu Pro Thr
45              50                  55                  60 tac gtg cgt tcc acc cca gaa ggc tca gaa gtc gga gac ttt ctc tcc         1624
Tyr Val Arg Ser Thr Pro Glu Gly Ser Glu Val Gly Asp Phe Leu Ser
                65                  70                  75 tta gac ctg gga gga acc aac ttc aga gtg atg ctg gtc aaa gtg gga         1672
Leu Asp Leu Gly Gly Thr Asn Phe Arg Val Met Leu Val Lys Val Gly
            80                  85                  90 gag ggg gag gca ggg cag tgg agc gtg aag aca aaa cac cag atg tac         1720
Glu Gly Glu Ala Gly Gln Trp Ser Val Lys Thr Lys His Gln Met Tyr
        95                  100                 105 tcc atc ccc gag gac gcc atg acg ggc act gcc gag atg ctc ttt gac         1768
Ser Ile Pro Glu Asp Ala Met Thr Gly Thr Ala Glu Met Leu Phe Asp
110                 115                 120 tac atc tct gaa tgc atc tct gac ttc ctt gac aag cat cag atg aag         1816
Tyr Ile Ser Glu Cys Ile Ser Asp Phe Leu Asp Lys His Gln Met Lys
125                 130                 135                 140 cac aag aaa ctg ccc ctg ggc ttc acc ttc tcc ttc cct gtg agg cac         1864
His Lys Lys Leu Pro Leu Gly Phe Thr Phe Ser Phe Pro Val Arg His
                145                 150                 155 gaa gac cta gac aag ggc atc ctc ctc aat tgg acc aag ggc ttc aag         1912
Glu Asp Leu Asp Lys Gly Ile Leu Leu Asn Trp Thr Lys Gly Phe Lys
            160                 165                 170 gcc tct gga gca gaa ggg aac aac atc gta gga ctt ctc cga gat gct         1960
Ala Ser Gly Ala Glu Gly Asn Asn Ile Val Gly Leu Leu Arg Asp Ala
        175                 180                 185 atc aag agg aga ggg gac ttt gag atg gat gtg gtg gca atg gtg aac         2008
Ile Lys Arg Arg Gly Asp Phe Glu Met Asp Val Val Ala Met Val Asn
    190                 195                 200 gac aca gtg gcc aca atg atc tcc tgc tac tat gaa gac cgc caa tgt         2056
Asp Thr Val Ala Thr Met Ile Ser Cys Tyr Tyr Glu Asp Arg Gln Cys
205                 210                 215                 220 gag gtc ggc atg att gtg ggc act ggc tgc aat gcc tgc tac atg gag         2104
Glu Val Gly Met Ile Val Gly Thr Gly Cys Asn Ala Cys Tyr Met Glu
                225                 230                 235 gaa atg cag aat gtg gag ctg gtg gaa ggg gat gag gga cgc atg tgc         2152
Glu Met Gln Asn Val Glu Leu Val Glu Gly Asp Glu Gly Arg Met Cys
            240                 245                 250 gtc aac acg gag tgg ggc gcc ttc ggg gac tcg ggc gag ctg gat gag         2200
Val Asn Thr Glu Trp Gly Ala Phe Gly Asp Ser Gly Glu Leu Asp Glu
        255                 260                 265
```

|  |  |
|---|---|
| ttc cta ctg gag tat gac cgg atg gtg gat gaa agc tca gcg aac ccc<br>Phe Leu Leu Glu Tyr Asp Arg Met Val Asp Glu Ser Ser Ala Asn Pro<br>    270                         275                        280 | 2248 |
| ggt cag cag ctg tac gag aag atc atc ggt ggg aag tat atg ggc gag<br>Gly Gln Gln Leu Tyr Glu Lys Ile Ile Gly Gly Lys Tyr Met Gly Glu<br>285                      290                        295                        300 | 2296 |
| ctg gta cga ctt gtg ctg ctt aag ctg gtg gac gag aac ctt ctg ttc<br>Leu Val Arg Leu Val Leu Leu Lys Leu Val Asp Glu Asn Leu Leu Phe<br>                         305                        310                        315 | 2344 |
| cac gga gag gcc tcg gag cag ctg cgc acg cgt ggt gct ttt gag acc<br>His Gly Glu Ala Ser Glu Gln Leu Arg Thr Arg Gly Ala Phe Glu Thr<br>                    320                        325                        330 | 2392 |
| cgt ttc gtg tca caa gtg gag agc gac tcc ggg gac cga aag cag atc<br>Arg Phe Val Ser Gln Val Glu Ser Asp Ser Gly Asp Arg Lys Gln Ile<br>               335                        340                        345 | 2440 |
| cac aac atc cta agc act ctg ggg ctt cga ccc tct gtc acc gac tgc<br>His Asn Ile Leu Ser Thr Leu Gly Leu Arg Pro Ser Val Thr Asp Cys<br>350                      355                        360 | 2488 |
| gac att gtg cgc cgt gcc tgt gaa agc gtg tcc act cgc gcc gcc cat<br>Asp Ile Val Arg Arg Ala Cys Glu Ser Val Ser Thr Arg Ala Ala His<br>365                      370                        375                        380 | 2536 |
| atg tgc tcc gca gga cta gct ggg gtc ata aat cgc atg cgc gaa agc<br>Met Cys Ser Ala Gly Leu Ala Gly Val Ile Asn Arg Met Arg Glu Ser<br>                    385                        390                        395 | 2584 |
| cgc agt gag gac gtg atg cgc atc act gtg ggc gtg gat ggc tcc gtg<br>Arg Ser Glu Asp Val Met Arg Ile Thr Val Gly Val Asp Gly Ser Val<br>               400                        405                        410 | 2632 |
| tac aag ctg cac ccg agc ttc aag gag cgg ttt cac gcc agt gtg cgc<br>Tyr Lys Leu His Pro Ser Phe Lys Glu Arg Phe His Ala Ser Val Arg<br>                    415                        420                        425 | 2680 |
| agg ctg aca ccc aac tgc gaa atc acc ttc atc gaa tca gag gag ggc<br>Arg Leu Thr Pro Asn Cys Glu Ile Thr Phe Ile Glu Ser Glu Glu Gly<br>               430                        435                        440 | 2728 |
| agc ggc agg gga gcc gca ctg gtc tct gcg gtg gcc tgc aag aag gct<br>Ser Gly Arg Gly Ala Ala Leu Val Ser Ala Val Ala Cys Lys Lys Ala<br>445                      450                        455                        460 | 2776 |
| tgc atg ctg gcc cag tga atccaggtc atatggaccg ggacctgggt<br>Cys Met Leu Ala Gln<br>               465 | 2824 |
| tccacgggga ctccacacac cacaaatgct cccagcccac cggggcagga gacctattct | 2884 |
| gctgctaccc ctggaaaatg gggagaggcc cctgcaagcc gagtcggcca gtgggacagc | 2944 |
| cctagggctc tcagcctggg gcaggggct gggaggaaga agaggatcag aggcgccaag | 3004 |
| gcctttcttg ctagaatcaa ctacagaaaa tggcggaaaa tactcaggac ttgcactttc | 3064 |
| acgattcttg cttcccaagc gtgggtctgg cctcccaagg gaatgcttcc tggaccttgc | 3124 |
| aatggcctgg cttccctggg ggggacacac cttcatgggg aggtaacttc agcagttcgg | 3184 |
| ccagaccaga ccccaggaga gtaagggctg ctagtcaccc agacctggct gttttcttgt | 3244 |
| ctgtggctga agaggccggg gagccatgag agactgacta ccggctaca tggagaggac | 3304 |
| tttccaggca tgaacatgcc agagactgtt gccttcatat acctccaccc gagtggctta | 3364 |
| cagttctggg atgaaccctc ccaggagatg ccagaggtta gagccccaga gtccttgctc | 3424 |
| taaggggacc agaaagggga ggcctcactc tgcactattc aagcaggaat catctccaac | 3484 |
| actcaggtcc ctgacccagg aggaagaagc caccctcagt gtccctccaa gagaccaccc | 3544 |
| aggtccttct ctccctcgtt cccaaatgcc agcctctcta cctgggactg tgggggagtt | 3604 |
| tttaattaaa tatttaaaac tacttcaaaa aaaaaaaaag gaattcacgc gtggtacctc | 3664 |

```
tagagtcgac ccgggcggcc gcttcccttt agtgagggtt aatgcttcga gcagacatga    3724
taagatacat tgatgagttt ggacaaacca caactagaat gcagtgaaaa aaatgcttta    3784
tttgtgaaat ttgtgatgct attgctttat ttgtaaccat tataagctgc aataaacaag    3844
ttaacaacaa caattgcatt cattttatgt ttcaggttca gggggagatg tgggaggttt    3904
tttaaagcaa gtaaaacctc tacaaatgtg gtaaaatccg ataagggact agagcatggc    3964
tacgtagata agtagcatgg cgggttaatc attaactaca aggaacccct agtgatggag    4024
ttggccactc cctctctgcg cgctcgctcg ctcactgagg ccgggcgacc aaaggtcgcc    4084
cgacgcccgg gctttgcccg gcggcctca gtgagcgagc gagcgcgc    4132
```

```
<210> SEQ ID NO 4
<211> LENGTH: 465
<212> TYPE: PRT
<213> ORGANISM: Artificial Sequence
<220> FEATURE:
<223> OTHER INFORMATION: Synthetic Construct

<400> SEQUENCE: 4

Met Ala Met Asp Thr Thr Arg Cys Gly Ala Gln Leu Leu Thr Leu Val
1               5                   10                  15

Glu Gln Ile Leu Ala Glu Phe Gln Leu Gln Glu Asp Leu Lys Lys
            20                  25                  30

Val Met Ser Arg Met Gln Lys Glu Met Asp Arg Gly Leu Arg Leu Glu
        35                  40                  45

Thr His Glu Glu Ala Ser Val Lys Met Leu Pro Thr Tyr Val Arg Ser
    50                  55                  60

Thr Pro Glu Gly Ser Glu Val Gly Asp Phe Leu Ser Leu Asp Leu Gly
65                  70                  75                  80

Gly Thr Asn Phe Arg Val Met Leu Val Lys Val Gly Glu Gly Glu Ala
                85                  90                  95

Gly Gln Trp Ser Val Lys Thr Lys His Gln Met Tyr Ser Ile Pro Glu
            100                 105                 110

Asp Ala Met Thr Gly Thr Ala Glu Met Leu Phe Asp Tyr Ile Ser Glu
        115                 120                 125

Cys Ile Ser Asp Phe Leu Asp Lys His Gln Met Lys His Lys Lys Leu
    130                 135                 140

Pro Leu Gly Phe Thr Phe Ser Phe Pro Val Arg His Glu Asp Leu Asp
145                 150                 155                 160

Lys Gly Ile Leu Leu Asn Trp Thr Lys Gly Phe Lys Ala Ser Gly Ala
                165                 170                 175

Glu Gly Asn Asn Ile Val Gly Leu Leu Arg Asp Ala Ile Lys Arg Arg
            180                 185                 190

Gly Asp Phe Glu Met Asp Val Val Ala Met Val Asn Asp Thr Val Ala
        195                 200                 205

Thr Met Ile Ser Cys Tyr Tyr Glu Asp Arg Gln Cys Glu Val Gly Met
    210                 215                 220

Ile Val Gly Thr Gly Cys Asn Ala Cys Tyr Met Glu Glu Met Gln Asn
225                 230                 235                 240

Val Glu Leu Val Glu Gly Asp Glu Gly Arg Met Cys Val Asn Thr Glu
                245                 250                 255

Trp Gly Ala Phe Gly Asp Ser Gly Glu Leu Asp Glu Phe Leu Leu Glu
            260                 265                 270

Tyr Asp Arg Met Val Asp Glu Ser Ser Ala Asn Pro Gly Gln Gln Leu
        275                 280                 285
```

```
Tyr Glu Lys Ile Ile Gly Gly Lys Tyr Met Gly Glu Leu Val Arg Leu
    290                 295                 300

Val Leu Leu Lys Leu Val Asp Glu Asn Leu Leu Phe His Gly Glu Ala
305                 310                 315                 320

Ser Glu Gln Leu Arg Thr Arg Gly Ala Phe Glu Thr Arg Phe Val Ser
                325                 330                 335

Gln Val Glu Ser Asp Ser Gly Asp Arg Lys Gln Ile His Asn Ile Leu
            340                 345                 350

Ser Thr Leu Gly Leu Arg Pro Ser Val Thr Asp Cys Asp Ile Val Arg
        355                 360                 365

Arg Ala Cys Glu Ser Val Ser Thr Arg Ala Ala His Met Cys Ser Ala
    370                 375                 380

Gly Leu Ala Gly Val Ile Asn Arg Met Arg Glu Ser Arg Ser Glu Asp
385                 390                 395                 400

Val Met Arg Ile Thr Val Gly Val Asp Gly Ser Val Tyr Lys Leu His
                405                 410                 415

Pro Ser Phe Lys Glu Arg Phe His Ala Ser Val Arg Arg Leu Thr Pro
            420                 425                 430

Asn Cys Glu Ile Thr Phe Ile Glu Ser Glu Glu Gly Ser Gly Arg Gly
        435                 440                 445

Ala Ala Leu Val Ser Ala Val Ala Cys Lys Lys Ala Cys Met Leu Ala
    450                 455                 460

Gln
465

<210> SEQ ID NO 5
<211> LENGTH: 2371
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1336)..(1668)

<400> SEQUENCE: 5
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120 actagggtt cctgcggccg cacgcgtgga gctagttatt aatagtaatc aattacgggg      180
tcattagttc atagcccata tatggagttc cgcgttacat aacttacggt aaatggcccg     240
cctggctgac cgcccaacga ccccgccca ttgacgtcaa taatgacgta tgttcccata      300
gtaacgtcaa tagggacttt ccattgacgt caatgggtgg agtatttacg gtaaactgcc     360
cacttggcag tacatcaagt gtatcatatg ccaagtacgc cccctattga cgtcaatgac     420
ggtaaatggc ccgcctggca ttatgcccag tacatgacct tatgggactt tcctacttgg     480
cagtacatct acgtattagt catcgctatt accatggtga tgcggttttg gcagtacatc     540
aatgggcgtg gatagcggtt tgactcacgg ggatttccaa gtctccaccc cattgacgtc     600
aatgggagtt gtttgcac caaaatcaac gggactttcc aaaatgtcgt aacaactccg      660
ccccattgac gcaaatgggc ggtaggcgtg tacggtggga ggtctatata agcagagctc     720
gtttagtgaa ccgtcagatc gcctggagac gccatccacg ctgttttgac ctccatagaa     780
gacacccgga ccgatccagc ctccgcggat tcgaatcccg gccgggaacg gtgcattgga     840
acgcggattc cccgtgccaa gagtgacgta agtaccgcct atagagtcta taggcccaca     900
```

```
aaaaatgctt tcttcttta atatactttt ttgtttatct tatttctaat actttcccta    960
atctctttct ttcagggcaa taatgataca atgtatcatg cctctttgca ccattctaaa   1020
gaataacagt gataatttct gggttaaggc aatagcaata tttctgcata taaatatttc   1080
tgcatataaa ttgtaactga tgtaagaggt ttcatattgc taatagcagc tacaatccag   1140
ctaccattct gcttttattt tatggttggg ataaggctgg attattctga gtccaagcta   1200
ggcccttttg ctaatcatgt tcatacctct tatcttcctc ccacagctcc tgggcaacgt   1260
gctggtctgt gtgctggccc atcactttgg caaagaattg ggattcgaac atcgattgaa   1320
```
ttcctcgagg ccacc atg gcc ctg tgg atg aga ctg ctg cct ctg ctg gcc    1371
              Met Ala Leu Trp Met Arg Leu Leu Pro Leu Leu Ala
                1               5                   10 ctg ctg gct ctg tgg ggc cct gac cct gcc gcc gct ttc gtg aac cag     1419
Leu Leu Ala Leu Trp Gly Pro Asp Pro Ala Ala Ala Phe Val Asn Gln
            15                  20                  25 cac ctg tgc ggc agc gat ctg gtg gag gcc ctg tac ctg gtc tgc ggc     1467
His Leu Cys Gly Ser Asp Leu Val Glu Ala Leu Tyr Leu Val Cys Gly
        30                  35                  40 gag aga ggc ttc ttc tac acc cct agg acc aag aga gag gcc gag gac     1515
Glu Arg Gly Phe Phe Tyr Thr Pro Arg Thr Lys Arg Glu Ala Glu Asp
 45              50                  55                  60 ctc cag gtc gga cag gtg gaa ctg ggc gga gga cct ggc gct gga tct     1563
Leu Gln Val Gly Gln Val Glu Leu Gly Gly Gly Pro Gly Ala Gly Ser
                65                  70                  75 ctg cag cct ctg gcc ctg gaa ggc agc aga cag aaa agg ggc atc gtg     1611
Leu Gln Pro Leu Ala Leu Glu Gly Ser Arg Gln Lys Arg Gly Ile Val
            80                  85                  90 gag cag tgc tgc acc agc atc tgc agc ctg tac cag ctg gaa aac tac     1659
Glu Gln Cys Cys Thr Ser Ile Cys Ser Leu Tyr Gln Leu Glu Asn Tyr
        95                  100                 105 tgc aac tga ggatccgtcg acctgcagaa gcttgcctcg agcagcgctg             1708
Cys Asn
    110

```
ctcgagagat ctacgggtgg catccctgtg acccctcccc agtgcctctc ctggccctgg   1768
aagttgccac tccagtgccc accagccttg tcctaataaa attaagttgc atcattttgt   1828
ctgactaggt gtccttctat aatattatgg ggtggagggg ggtggtatgg agcaaggggc   1888
aagttgggaa gacaacctgt agggcctgcg ggtctattg  gaaccaagc tggagtgcag    1948 tggcacaatc ttggctcact gcaatctccg cctcctgggt tcaagcgatt ctcctgcctc   2008
agcctcccga gttgttggga ttccaggcat gcatgaccag gctcagctaa ttttgtttt    2068 tttggtagag acgggtttc accatattgg ccaggctggt ctccaactcc taatctcagg    2128
tgatctaccc accttggcct cccaaattgc tgggattaca ggcgtgaacc actgctccct   2188
tccctgtcct tctgattttg taggtaacca cgtgcggacc gagcggccgc aggaacccct   2248
agtgatggag ttggccactc cctctctgcg cgctcgctcg ctcactgagg ccgggcgacc   2308
aaaggtcgcc cgacgcccgg gctttgcccg ggcggcctca gtgagcgagc gagcgcgcag   2368
ctg                                                                2371
```

<210> SEQ ID NO 6
<211> LENGTH: 110
<212> TYPE: PRT
<213> ORGANISM: Artificial Sequence
<220> FEATURE:
<223> OTHER INFORMATION: Synthetic Construct

<400> SEQUENCE: 6

```
Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser Asp Leu Val Glu Ala Leu Tyr Leu Val Cys Gly Glu Arg Gly Phe
        35                  40                  45

Phe Tyr Thr Pro Arg Thr Lys Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Arg Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```

<210> SEQ ID NO 7
<211> LENGTH: 3454
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1344)..(2744)

<400> SEQUENCE: 7

| | |
|---|---:|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccgca cgcgtggagc tagttattaa tagtaatcaa | 180 |
| ttacggggtc attagttcat agcccatata tggagttccg cgttacataa cttacggtaa | 240 |
| atggcccgcc tggctgaccg cccaacgacc cccgcccatt gacgtcaata atgacgtatg | 300 |
| ttcccatagt aacgtcaata gggactttcc attgacgtca atgggtggag tatttacggt | 360 |
| aaactgccca cttggcagta catcaagtgt atcatatgcc aagtacgccc cctattgacg | 420 |
| tcaatgacgg taaatggccc gcctggcatt atgcccagta catgacctta tgggactttc | 480 |
| ctacttggca gtacatctac gtattagtca tcgctattac catggtgatg cggttttggc | 540 |
| agtacatcaa tgggcgtgga tagcggtttg actcacgggg atttccaagt ctccacccca | 600 |
| ttgacgtcaa tgggagtttg ttttgcacca aaatcaacgg gactttccaa aatgtcgtaa | 660 |
| caactccgcc ccattgacgc aaatgggcgg taggcgtgta cggtgggagg tctatataag | 720 |
| cagagctcgt ttagtgaacc gtcagatcgc ctggagacgc catccacgct gttttgacct | 780 |
| ccatagaaga caccgggacc gatccagcct ccgcggattc gaatcccggc cgggaacggt | 840 |
| gcattggaac gcggattccc cgtgccaaga gtgacgtaag taccgcctat agagtctata | 900 |
| ggcccacaaa aaatgctttc ttcttttaat atactttttt gtttatctta tttctaatac | 960 |
| tttccctaat ctctttcttt cagggcaata atgatacaat gtatcatgcc tctttgcacc | 1020 |
| attctaaaga ataacagtga aatttctgg gttaaggcaa tagcaatatt tctgcatata | 1080 |
| aatatttctg catataaatt gtaactgatg taagaggttt catattgcta atagcagcta | 1140 |
| caatccagct accattctgc ttttatttta tggttgggat aaggctggat tattctgagt | 1200 |
| ccaagctagg cccttttgct aatcatgttc atacctctta tcttcctccc acagctcctg | 1260 |
| ggcaacgtgc tggtctgtgt gctggcccat cactttggca agaattgggg attcgaacat | 1320 |

```
cgattgaatt cctcgaggcc acc atg gct atg gac gtg acc aga agc cag gcc        1373
                         Met Ala Met Asp Val Thr Arg Ser Gln Ala
                         1               5                   10 cag acc gcc ctg aca ctg gtg gag cag atc ctg gcc gag ttc cag ctg          1421
Gln Thr Ala Leu Thr Leu Val Glu Gln Ile Leu Ala Glu Phe Gln Leu
                15                  20                  25 caa gaa gag gac ctg aag aaa gtg atg cgg cgg atg cag aaa gag atg          1469
Gln Glu Glu Asp Leu Lys Lys Val Met Arg Arg Met Gln Lys Glu Met
            30                  35                  40 gac aga ggc ctg aga ctg gaa acc cac gaa gag gcc agc gtg aag atg          1517
Asp Arg Gly Leu Arg Leu Glu Thr His Glu Glu Ala Ser Val Lys Met
        45                  50                  55 ctg ccc acc tac gtg cgg agc acc cct gag ggc agc gaa gtg ggc gac          1565
Leu Pro Thr Tyr Val Arg Ser Thr Pro Glu Gly Ser Glu Val Gly Asp
    60                  65                  70 ttc ctg agc ctg gac ctg ggc ggc acc aac ttc aga gtg atg ctg gtc          1613
Phe Leu Ser Leu Asp Leu Gly Gly Thr Asn Phe Arg Val Met Leu Val
75                  80                  85                  90 aaa gtg ggc gag ggc gaa gag gga cag tgg agc gtg aaa aca aag cac          1661
Lys Val Gly Glu Gly Glu Glu Gly Gln Trp Ser Val Lys Thr Lys His
                    95                  100                 105 cag atg tac agc atc ccc gag gac gcc atg aca ggc acc gcc gag atg          1709
Gln Met Tyr Ser Ile Pro Glu Asp Ala Met Thr Gly Thr Ala Glu Met
                110                 115                 120 ctg ttc gac tac atc agc gag tgt atc tcc gac ttc ctg gac aaa cat          1757
Leu Phe Asp Tyr Ile Ser Glu Cys Ile Ser Asp Phe Leu Asp Lys His
            125                 130                 135 cag atg aag cac aag aag ctg ccc ctg ggc ttc acc ttc agc ttc ccc          1805
Gln Met Lys His Lys Lys Leu Pro Leu Gly Phe Thr Phe Ser Phe Pro
        140                 145                 150 gtg cgg cac gag gac atc gac aag ggc atc ctg ctg aac tgg acc aag          1853
Val Arg His Glu Asp Ile Asp Lys Gly Ile Leu Leu Asn Trp Thr Lys
155                 160                 165                 170 ggc ttc aag gcc agc ggc gct gag ggc aac aac gtg gtc ggc ctg ctg          1901
Gly Phe Lys Ala Ser Gly Ala Glu Gly Asn Asn Val Val Gly Leu Leu
                    175                 180                 185 agg gac gcc atc aag aga aga ggc gac ttc gag atg gac gtg gtg gcc          1949
Arg Asp Ala Ile Lys Arg Arg Gly Asp Phe Glu Met Asp Val Val Ala
                190                 195                 200 atg gtc aac gat acc gtg gct acc atg atc agc tgc tac tac gag gac          1997
Met Val Asn Asp Thr Val Ala Thr Met Ile Ser Cys Tyr Tyr Glu Asp
            205                 210                 215 cac cag tgt gaa gtg ggc atg atc gtg ggc acc ggc tgc aac gcc tgc          2045
His Gln Cys Glu Val Gly Met Ile Val Gly Thr Gly Cys Asn Ala Cys
        220                 225                 230 tac atg gaa gag atg cag aac gtg gaa ctc gtg gag gga gat gag ggc          2093
Tyr Met Glu Glu Met Gln Asn Val Glu Leu Val Glu Gly Asp Glu Gly
235                 240                 245                 250 aga atg tgc gtg aac acc gag tgg ggc gcc ttc gga gac tct ggc gag          2141
Arg Met Cys Val Asn Thr Glu Trp Gly Ala Phe Gly Asp Ser Gly Glu
                    255                 260                 265 ctg gac gag ttc ctg ctg gaa tac gac aga ctg gtg gac gag agc agc          2189
Leu Asp Glu Phe Leu Leu Glu Tyr Asp Arg Leu Val Asp Glu Ser Ser
                270                 275                 280 gct aac ccc ggc cag cag ctg tac gag aag ctg atc ggc ggc aag tac          2237
Ala Asn Pro Gly Gln Gln Leu Tyr Glu Lys Leu Ile Gly Gly Lys Tyr
            285                 290                 295 atg gga gag ctg gtc cgg ctg gtg ctg ctg agg ctg gtg gat gag aac          2285
Met Gly Glu Leu Val Arg Leu Val Leu Leu Arg Leu Val Asp Glu Asn
        300                 305                 310
```

```
ctg ctg ttc cac ggc gag gcc tcc gag cag ctg aga acc aga ggc gcc    2333
Leu Leu Phe His Gly Glu Ala Ser Glu Gln Leu Arg Thr Arg Gly Ala
315                 320                 325                 330 ttc gaa acc aga ttc gtg agc cag gtg gag agc gac acc ggc gac aga    2381
Phe Glu Thr Arg Phe Val Ser Gln Val Glu Ser Asp Thr Gly Asp Arg
            335                 340                 345 aag cag atc tac aac atc ctg agc acc ctg ggc ctg agg cct agc acc    2429
Lys Gln Ile Tyr Asn Ile Leu Ser Thr Leu Gly Leu Arg Pro Ser Thr
350                 355                 360 acc gac tgc gac atc gtg cgg aga gcc tgc gag agc gtg tcc acc aga    2477
Thr Asp Cys Asp Ile Val Arg Arg Ala Cys Glu Ser Val Ser Thr Arg
            365                 370                 375 gcc gcc cac atg tgt tct gcc gga ctg gca ggc gtg atc aac aga atg    2525
Ala Ala His Met Cys Ser Ala Gly Leu Ala Gly Val Ile Asn Arg Met
380                 385                 390 cgg gag agc aga tcc gag gac gtg atg aga atc acc gtg ggc gtg gac    2573
Arg Glu Ser Arg Ser Glu Asp Val Met Arg Ile Thr Val Gly Val Asp
395                 400                 405                 410 ggc agc gtg tac aag ctg cac ccc agc ttc aaa gag cgg ttc cac gcc    2621
Gly Ser Val Tyr Lys Leu His Pro Ser Phe Lys Glu Arg Phe His Ala
            415                 420                 425 tcc gtg aga agg ctg acc ccc agc tgc gag atc acc ttc atc gag agc    2669
Ser Val Arg Arg Leu Thr Pro Ser Cys Glu Ile Thr Phe Ile Glu Ser
430                 435                 440 gag gaa ggc tct ggc aga ggc gcc gct ctg gtg tct gcc gtg gcc tgc    2717
Glu Glu Gly Ser Gly Arg Gly Ala Ala Leu Val Ser Ala Val Ala Cys
            445                 450                 455 aag aaa gcc tgc atg ctg ggc cag tga ggatccgtcg acctgcagaa          2764
Lys Lys Ala Cys Met Leu Gly Gln
    460                 465 gcttgcctcg agcagcgctg ctcgagagat ctacgggtgg catccctgtg accctcccc   2824 agtgcctctc ctggccctgg aagttgccac tccagtgccc accagccttg tcctaataaa  2884
attaagttgc atcattttgt ctgactaggt gtccttctat aatattatgg ggtgaggggg  2944
ggtggtatgg agcaaggggc aagttgggaa gacaacctgt agggcctgcg ggtctattg   3004 ggaaccaagc tggagtgcag tggcacaatc ttggctcact gcaatctccg cctcctgggt  3064
tcaagcgatt ctcctgcctc agcctcccga gttgttggga ttccaggcat gcatgaccag  3124
gctcagctaa ttttgtttt tttggtagag acggggtttc accatattgg ccaggctggt   3184
ctccaactcc taatctcagg tgatctaccc accttggcct cccaaattgc tgggattaca  3244
ggcgtgaacc actgctccct tccctgtcct tctgattttg taggtaacca cgtgcggacc  3304
gagcggccgc aggaacccct agtgatggag ttggccactc cctctctgcg cgctcgctcg  3364
ctcactgagg ccgggcgacc aaaggtcgcc cgacgcccgg gctttgcccg ggcggcctca  3424
gtgagcgagc gagcgcgcag ctgcctgcag                                   3454
```

<210> SEQ ID NO 8
<211> LENGTH: 466
<212> TYPE: PRT
<213> ORGANISM: Artificial Sequence
<220> FEATURE:
<223> OTHER INFORMATION: Synthetic Construct

<400> SEQUENCE: 8

```
Met Ala Met Asp Val Thr Arg Ser Gln Ala Gln Thr Ala Leu Thr Leu
1               5                   10                  15

Val Glu Gln Ile Leu Ala Glu Phe Gln Leu Gln Glu Glu Asp Leu Lys
            20                  25                  30
```

```
Lys Val Met Arg Arg Met Gln Lys Glu Met Asp Arg Gly Leu Arg Leu
         35                  40                  45
Glu Thr His Glu Glu Ala Ser Val Lys Met Leu Pro Thr Tyr Val Arg
 50                      55                  60
Ser Thr Pro Glu Gly Ser Glu Val Gly Asp Phe Leu Ser Leu Asp Leu
 65                  70                  75                  80
Gly Gly Thr Asn Phe Arg Val Met Leu Val Lys Val Gly Glu Gly Glu
                     85                  90                  95
Glu Gly Gln Trp Ser Val Lys Thr Lys His Gln Met Tyr Ser Ile Pro
             100                 105                 110
Glu Asp Ala Met Thr Gly Thr Ala Glu Met Leu Phe Asp Tyr Ile Ser
         115                 120                 125
Glu Cys Ile Ser Asp Phe Leu Asp Lys His Gln Met Lys His Lys Lys
         130                 135                 140
Leu Pro Leu Gly Phe Thr Phe Ser Phe Pro Val Arg His Glu Asp Ile
145                 150                 155                 160
Asp Lys Gly Ile Leu Leu Asn Trp Thr Lys Gly Phe Lys Ala Ser Gly
                 165                 170                 175
Ala Glu Gly Asn Asn Val Val Gly Leu Leu Arg Asp Ala Ile Lys Arg
             180                 185                 190
Arg Gly Asp Phe Glu Met Asp Val Val Ala Met Val Asn Asp Thr Val
         195                 200                 205
Ala Thr Met Ile Ser Cys Tyr Tyr Glu Asp His Gln Cys Glu Val Gly
         210                 215                 220
Met Ile Val Gly Thr Gly Cys Asn Ala Cys Tyr Met Glu Glu Met Gln
225                 230                 235                 240
Asn Val Glu Leu Val Glu Gly Asp Glu Gly Arg Met Cys Val Asn Thr
                 245                 250                 255
Glu Trp Gly Ala Phe Gly Asp Ser Gly Glu Leu Asp Glu Phe Leu Leu
             260                 265                 270
Glu Tyr Asp Arg Leu Val Asp Glu Ser Ser Ala Asn Pro Gly Gln Gln
         275                 280                 285
Leu Tyr Glu Lys Leu Ile Gly Gly Lys Tyr Met Gly Glu Leu Val Arg
         290                 295                 300
Leu Val Leu Leu Arg Leu Val Asp Glu Asn Leu Leu Phe His Gly Glu
305                 310                 315                 320
Ala Ser Glu Gln Leu Arg Thr Arg Gly Ala Phe Glu Thr Arg Phe Val
                 325                 330                 335
Ser Gln Val Glu Ser Asp Thr Gly Asp Arg Lys Gln Ile Tyr Asn Ile
             340                 345                 350
Leu Ser Thr Leu Gly Leu Arg Pro Ser Thr Thr Asp Cys Asp Ile Val
         355                 360                 365
Arg Arg Ala Cys Glu Ser Val Ser Thr Arg Ala Ala His Met Cys Ser
         370                 375                 380
Ala Gly Leu Ala Gly Val Ile Asn Arg Met Arg Glu Ser Arg Ser Glu
385                 390                 395                 400
Asp Val Met Arg Ile Thr Val Gly Val Asp Gly Ser Val Tyr Lys Leu
                 405                 410                 415
His Pro Ser Phe Lys Glu Arg Phe His Ala Ser Val Arg Arg Leu Thr
             420                 425                 430
Pro Ser Cys Glu Ile Thr Phe Ile Glu Ser Glu Glu Gly Ser Gly Arg
         435                 440                 445
```

```
Gly Ala Ala Leu Val Ser Ala Val Ala Cys Lys Lys Ala Cys Met Leu
    450                 455                 460
Gly Gln
465
```

GENE THERAPY COMPOSITION FOR USE IN DIABETES TREATMENT

CROSS-REFERENCE TO RELATED APPLICATIONS

This application is filed under the provisions of 35 U.S.C. § 120 and is a continuation application claiming priority to co-pending U.S. patent application Ser. No. 13/809,777, filed on May 29, 2013, which was filed under the provisions 35 U.S.C. § 371 and claims the priority of International Patent Application No. PCT/EP2011/061487 filed on 12 Jul. 2011 entitled "GENE THERAPY COMPOSITION FOR USE IN DIABETES TREATMENT" in the name of Fátima BOSCH TUBERT, et al., which claims priority to European Patent Application No. 10169309.1 filed on 12 Jul. 2010, all of which are hereby incorporated by reference in their entirety.

FIELD OF THE INVENTION

The invention pertains to the medical field, comprising gene therapy compositions for use in the treatment of Diabetes Type 1 or 2 (T1D or T2D), either in higher mammals, particularly pets and more particularly dogs; or in human beings.

STATE OF THE ART

The two main forms of diabetes mellitus are type 1 (T1D) and type 2 (T2D) (1). T1D is characterized by a severe lack of insulin production due to specific destruction of the pancreatic β-cells. β-cell loss in T1D is the result of an autoimmune mediated process, where a chronic inflammation called insulitis causes β-cell destruction (2, 3).

T1D is one of the most common endocrine and metabolic conditions in childhood; incidence is rapidly increasing, especially among young children. T1D is diagnosed when the autoimmune-mediated β-cell destruction is almost complete and patients need insulin-replacement therapy to survive. T1D in an adult may present itself as T2D, with a slow deterioration in metabolic control, and subsequent progression to insulin dependency. This form is called latent autoimmune diabetes mellitus in adults (LADA) (6).

Lifelong insulin treatment is the therapy of choice for T1D. While lifelong treatment with exogenous insulin successfully manages diabetes, correct maintenance of a normoglycemic state can be challenging, Chronic hyperglycemia leads to severe microvascular (retinopathy and nephropathy), macrovascular (stroke, myocardial infarction), and neurological complications. These devastating complications can be prevented by normalization of blood glucose levels. Brittle diabetes is one example of a difficult-to-manage disease. Additionally, in many underdeveloped countries, especially in less privileged families, access to self-care tools and also to insulin is limited and this may lead to severe handicap and early death in diabetic children (6-8). The most common cause of death in a child with diabetes, from a global perspective, is lack of access to insulin; thus the availability of a one-time gene therapy approach could make a difference in terms of prognosis when access to insulin is limited (9).

The reduction of hyperglycemia and maintenance of normoglycemia is a goal of any therapeutic approach to T1D. The current therapy for most diabetic patients is based on regular subcutaneous injections of mixtures of soluble (short-acting) insulin and lente (long-acting) insulin preparations. Suspensions of soluble insulin particles of different size that give intermediate acting and long-acting components with more sustained action profiles are administered to achieve a constant basal level of the hormone (10). However, one of the major deficiencies of delayed-action insulin is the variable absorption from subcutaneous tissue (11), mainly because the formulation is a suspension. Moreover, the delayed-action preparations do not generally produce smooth background levels of insulin, resulting in either hyperglycemia or hypoglycemia. Intensive insulin therapy can delay the onset and slow the progression of retinopathy, nephropathy, and neuropathy in T1D patients (12). However, this kind of treatment is not suitable for all diabetic patients, especially the very young or the old ones. In addition, patients under intensive insulin treatment present a high risk for hypoglycemia. Hypoglycemia is caused by inappropriately raised insulin concentrations or enhanced insulin effect, because of excessive insulin dosage, increased bioavailability, increased sensitivity, and/or inadequate carbohydrate intake (13, 14).

To maintain normoglycemia, especially in cases of brittle diabetes, a form of diabetes not easily managed with exogenous insulin administration, one alternative approach is cell-based therapy that involves transplantation of pancreatic islets or β-cells mainly from cadaveric donors. While some clinical success has been achieved with this approach, particularly with the Edmonton protocol (15, 16), there are still considerable obstacles to be overcome before these strategies will achieve widespread clinical acceptance and improved long-lasting efficacy. In particular, transplanted patients must receive life-long immunosuppression to avoid graft rejection, while the existing autoimmunity (the underlying cause of diabetes) may contribute to diminished graft survival or limit effectiveness of this treatment approach to only a few years at most (17). Another limitation of the approach comes from the fact that several donors are needed to treat a single patient. As a possible solution to the limited availability of human islets, pig islets may offer an abundant source of tissue and encapsulated islets have been xenotransplanted to non-human primates and, recently, to humans (18, 19). However, in addition to lack of long-term efficacy in terms of insulin production and the obvious safety concerns related to the use of non-human material that may carry unknown infectious diseases, the use of pig islets face difficulties for health authorities' regulatory approval and general public aversion. Also stem cell-based technologies have emerged in recent years as a possible approach to treat diabetes; besides issues related to the underlying autoimmune disease, which may require lifelong immunosuppression, these technologies are still too young to see them applied in the clinical arena in the next few years. Thus, while clinical and research efforts are needed to improve existing therapeutic strategies, it is clear that there is considerable need for new alternative approaches for the treatment of T1D.

To maintain normoglycemia, studies have also focused on the use of surrogate non-β-cells to deliver insulin (20, 21). These approaches aim to lower blood glucose by delivering insulin under the control of glucose-responsive promoters, such as pyruvate kinase in the liver (22). However, the slow transcriptional control by glucose delays the insulin secretory response, which may lead to hyperglycemia immediately after meals and to hypoglycemia several hours later. To some extent, this can be circumvented by the use of cells that process and store insulin, such as gut K cells (23), or by inducing β-cell neogenesis in the liver by expression of key transcription factors (24, 25). These strategies present other restrictions, such as feasibility, safety and long-term efficacy.

Unlike conventional insulin replacement therapy, gene therapy would offer the potential advantage of a single viral vector administration, which could ideally provide the necessary insulin through the lifetime of the diabetic subject.

To develop an alternative approach to diabetes therapy, the inventors had previously examined the ability of genetic manipulation of skeletal muscle to counteract diabetic hyperglycemia. Skeletal muscle is the most important site of glucose removal from blood, accounting for about 70% of glucose disposal after a meal. In addition, skeletal muscle is an excellent target tissue for gene transfer because of its accessibility and its capacity to secrete proteins. Glucose utilization by skeletal muscle is controlled by insulin-stimulated glucose transport through GLUT4 (26) and its phosphorylation by hexokinase II (HK-II) (27). HK-II has a low Km for glucose and is inhibited by glucose-6-phosphate, which limits glucose uptake. During diabetes, because of the lack of insulin, GLUT4 translocation to the plasma membrane and HKII mRNA levels and activity are decrease (28, 29). Expression of basal levels of insulin in skeletal muscle of transgenic mice increases glucose uptake (30), since insulin receptors are widely distributed in muscle fibers (31). When diabetic, insulin-expressing transgenic mice are normoglycemic during fasting but remain hyperglycemic in fed conditions (30). To increase glucose phosphorylation, the hepatic glucose phosphorylating enzyme Gck has also been expressed in skeletal muscle (32). In contrast to HK-II, Gck has a high Km for glucose (about 8 mM), it is not inhibited by glucose 6-phosphate, and it shows kinetic cooperativity with glucose (27). These features allow glucose to be taken up only when it is at high concentrations, as already reported in pancreatic β-cells (33). Expression of Gck in skeletal muscle increases glucose disposal and reduces diabetic hyperglycemia (32, 34, 35). However, expression of Gck alone cannot normalize glycemia in type 1 diabetes because of the lack of insulin-mediated glucose transport. In this regard, we have found that the expression of Gck in skeletal muscle of fed diabetic transgenic mice in conjunction with the administration of low doses of soluble, short acting, insulin leads to the normalization of glycemia (32).

The invention departs from the hypothesis that basal production of insulin, by genetically engineered skeletal muscle, may provide the levels of insulin required to maintain normoglycemia between meals. After feeding, blood glucose levels rise and the insulin produced by skeletal muscle, acting in an autocrine/paracrine manner, may lead to GLUT4 translocation to plasma membrane and glucose transport into muscle fibers while expression of Gck may increase glucose utilization and normalization of glycemia. Thus, an approach combining insulin and Gck may prevent chronic hyperglycemia and avoid hypoglycemic events. In this regard, the inventors have recently shown that co-expression of Gck and insulin in mouse skeletal muscle reverts diabetic alterations (36). Double transgenic mice expressing both Gck and insulin in skeletal muscle counteract hyperglycemia and restores fluid and food intake after treatment with streptozotocin.

The inventors have also demonstrated in the past the feasibility of this approach in T1D mice by using Adeno-associated virus (AAV)-based vectors of serotype 1 (AAV1) to transfer the insulin and Gck genes into skeletal muscle of diabetic mice (36). AAV vectors are one of the preferred tools for gene transfer. The high transduction efficiency in vivo in a variety of post-mitotic tissues and the relatively low immunogenicity contributed to the AAV vectors use in a variety of preclinical studies (37). Translation of preclinical results into the clinical arena resulted in promising results (38-44), confirming the ability of AAV vectors to safely transduce liver, muscle, and neurological tissue in humans. Importantly, several groups showed that a single administration of AAV vectors to the liver, muscle, retina, and other tissues leads to long-term expression of the transgene product (45-47).

The inventors previously disclosed that expression of Gck and insulin genes into skeletal muscle of diabetic mice by using AAV1 vectors leads to complete normalization of glycemia (36). In addition, these mice present normal blood glucose levels when fasted and hypoglycemia is not observed. Insulin+Gck-treated diabetic mice also show increased skeletal muscle glucose uptake, normalization of liver glucose metabolism (increased glucose uptake and glycogen synthesis and reduced hepatic glucose production) and glucose tolerance test. Moreover, these mice present with normal food and fluid intake and normalization of abdominal fat pad and skeletal muscle weights. These results suggest that secretion of basal levels of insulin, in conjunction with increased glucose uptake by the skeletal muscle, may permit tight regulation of glycemia (36). Furthermore, in contrast to diabetic non-treated mice, preliminary results suggest that normalization of glycemia in Insulin+Gck-treated diabetic mice prevented development of secondary complications. However, there is still need of gene therapy compositions that may be proven useful in the treatment of diabetes in mammals of higher taxonomy, like pets (dogs) or even human beings.

T1D is one of the most common endocrine and metabolic conditions in childhood; T1D is diagnosed when the auto-immune-mediated β-cell destruction is almost complete and patients need insulin-replacement therapy to survive. T2D results from the reduced ability of the pancreatic β-cells to secrete enough insulin to stimulate glucose utilization by peripheral tissues; defects in both insulin secretion and action contribute to the pathogenesis of T2D, but it is now recognized that insulin deficiency is crucial to T2D pathogenesis. While lifelong treatment with exogenous insulin successfully manages diabetes, correct maintenance of a normoglycemic state can be challenging, exposing diabetic patients to life threatening hypoglycemia and long-term complications of hyperglycemia. Sub-optimal regulation of glycemia leads to severe microvascular (retinopathy and nephropathy), macrovascular (stroke, myocardial infarction), and neurological complications, which are hallmarks of both T1D and T2D. Alternative strategies involving transplantation of pancreatic islets or β-cells, present still considerable obstacles to overcome before they achieve widespread clinical acceptance and improved long-lasting efficacy, probably including life-long immunosuppression to avoid graft rejection.

SUMMARY OF THE INVENTION

The invention herein presents an innovative alternative to treat T1D and T2D, based on gene therapy delivered to the skeletal muscle to counteract diabetic hyperglycemia. Muscle was selected as target tissue due to his easy accessibility, capacity to secrete proteins and because of its relevance in the pathophisiology of diabetes, being accountable for about a 70% of glucose disposal after a meal.

Adeno-associated viral vectors (AAV1) were selected as vehicles for delivering insulin and glucokinase genes into the muscle tissue (local delivery). These vectors have proven to be safe and are already used in clinical testing (38, 44).

Basal production of insulin, by genetically engineered skeletal muscle, may provide the levels of insulin required to maintain normoglycemia between meals. After feeding, blood glucose levels rise and the insulin produced by skeletal muscle, acting in an autocrine/paracrine manner, may lead to GLUT4 translocation to plasma membrane and glucose transport into muscle fibers, while expression of Gck may increase glucose utilization and normalization of glycemia. Thus, an approach combining insulin and Gck may prevent chronic hyperglycemia and avoid hypoglycemic events. This approach was shown to be effective to normalize glycemia in diabetic mice (36).

Figure 19:
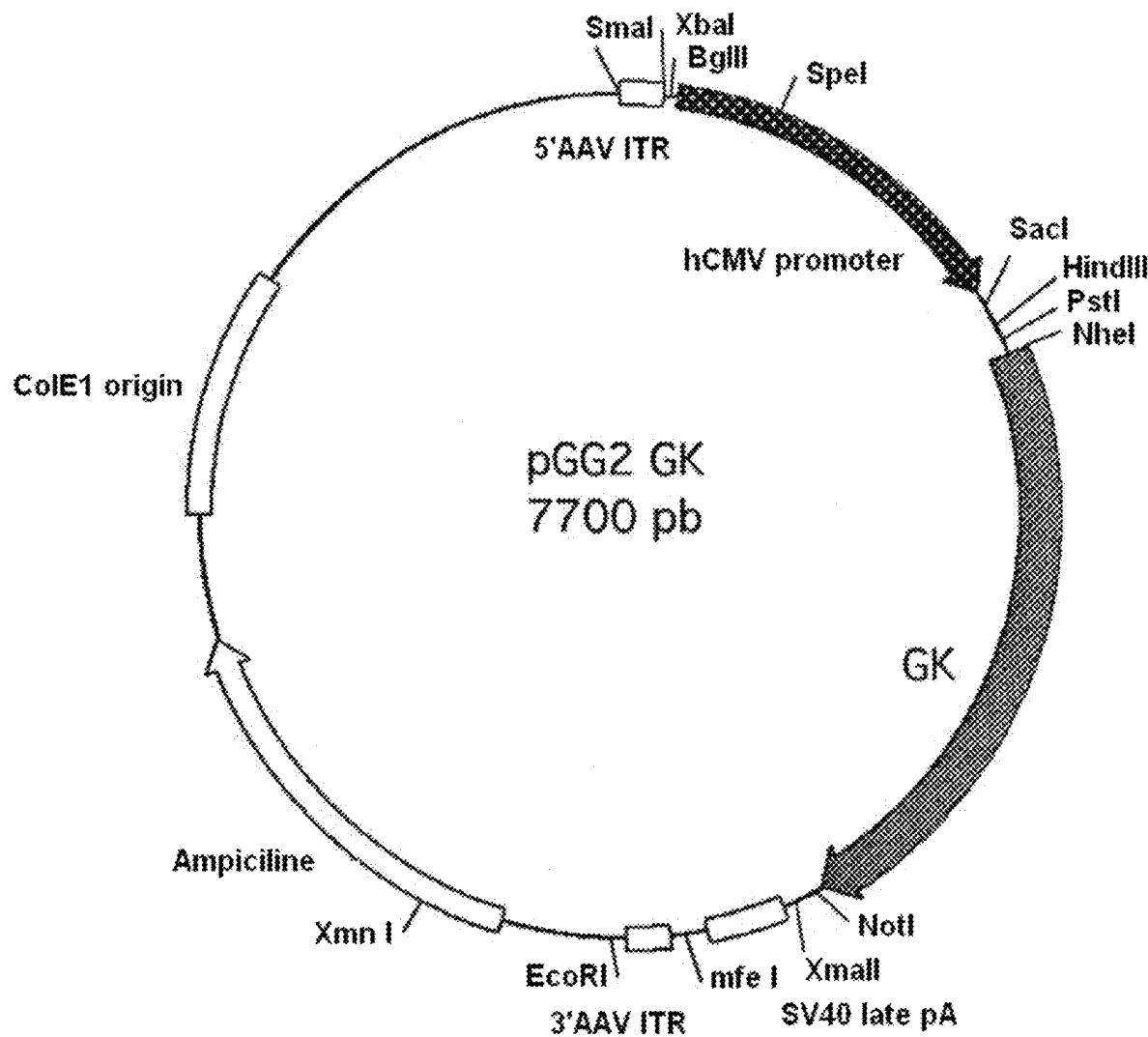
Figure 20:
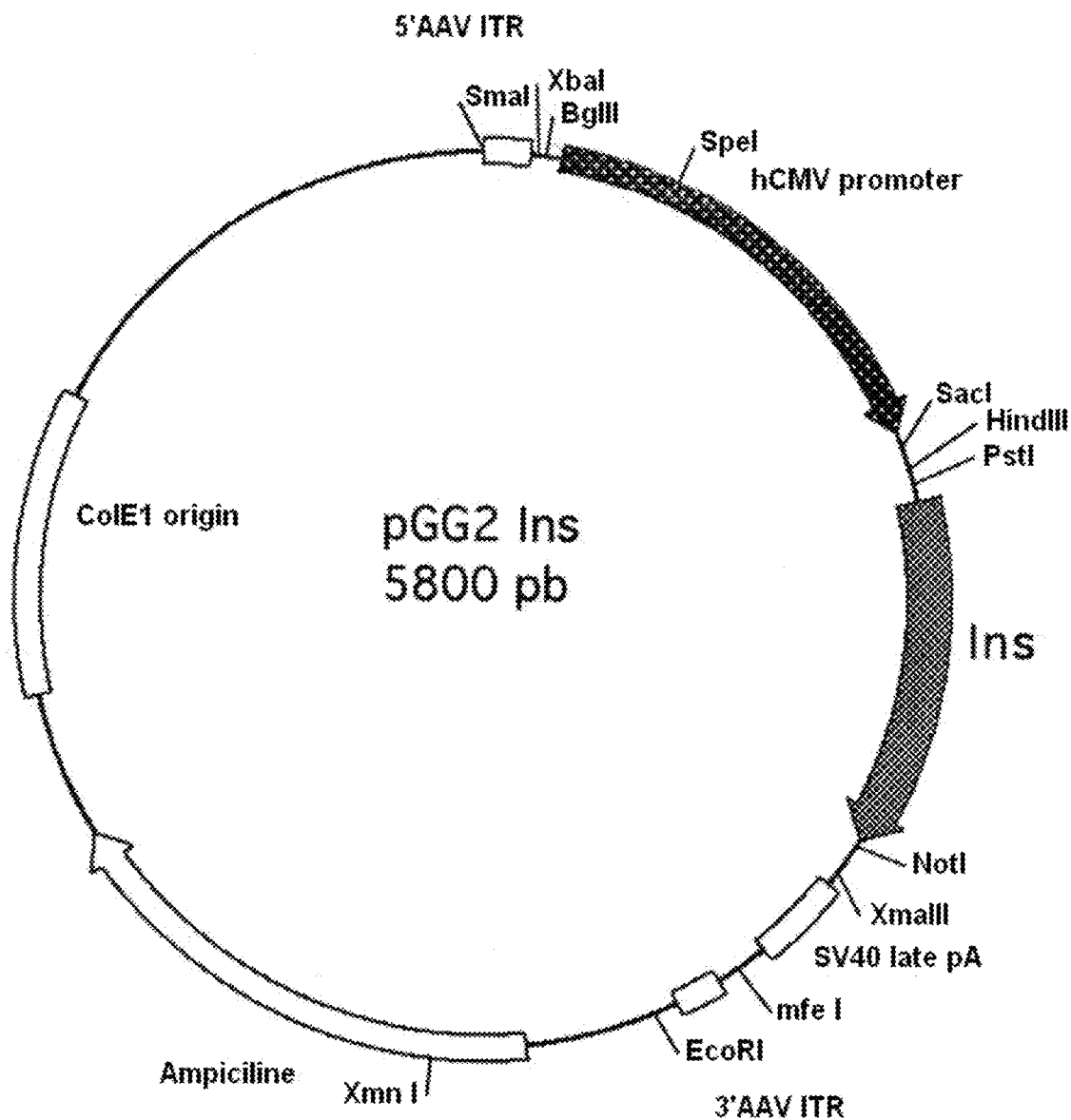

The invention shows, by experiments carried out in Beagle dogs, that a single administration of AAV1-human insulin (vector that comprises the human insulin sequence gene cloned in the pGG2 plasmid, resulting in the plasmido pGG2hIns, FIG. 20) and AAV1-rat glucokinase (vector that comprises the human glucokinase sequence gene cloned in the pGG2 plasmid, resulting in the plasmido pGG2hGcK, FIG. 19) (AAV1-hIns, AAV1-rGck, respectively) was able to normalize fasting plasma glucose and improve glucose disposal after oral glucose tolerance test, for periods of time longer than 2 years. Normalization of body weight and elevated liver enzymes was also achieved in one dog with severe diabetes. Serious adverse events have not been observed in all (five) animals treated, suggesting a good safety profile of this approach. In conclusion, the invention shows that expression of human insulin and rat Gck in skeletal muscle is a valuable and safe approach that allows long-term survival in animal suffering from diabetes for long time (>2 years); along with body weight maintenance, normal physical performance and normalization of serum parameters.

Figure 5:
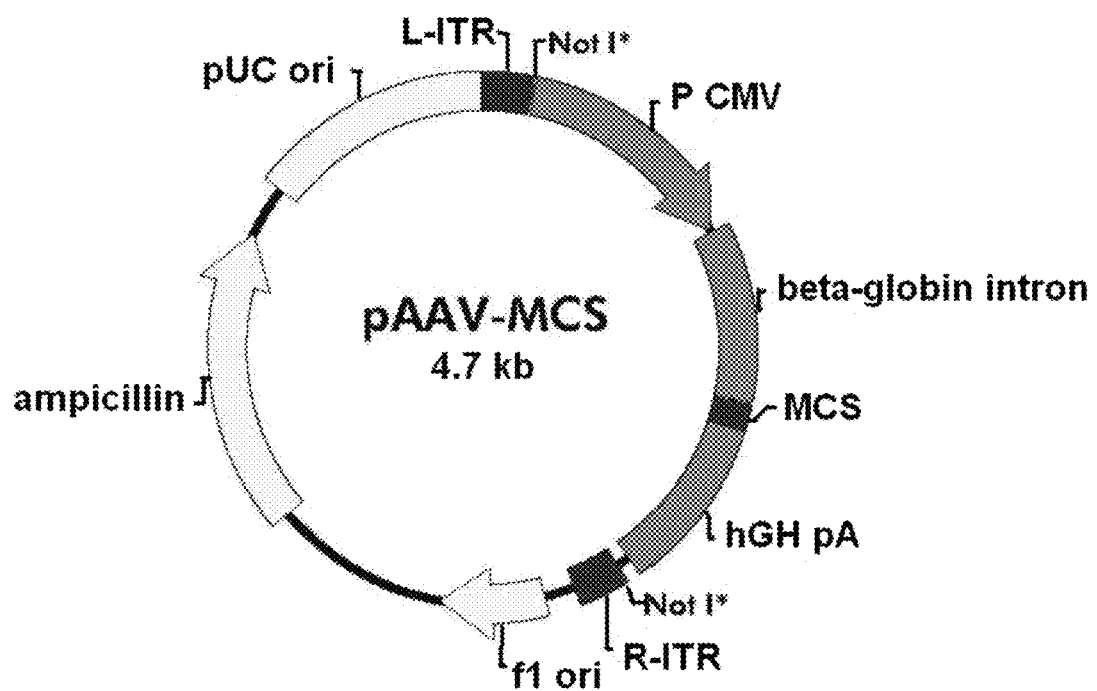

Additionally, the present invention also discloses that a single administration of AAV-mhIns (vector that comprises the mutated human insulin sequence gene cloned in the pAAV-MCS plasmid, FIG. 5, resulting in the plasmid pAAVmhINS) and AAV-mhGcK (vector that comprises the human glucokinase sequence gene cloned in the pAAV-MCS plasmid, FIG. 5, resulting in the plasmid pAAVmhGcK) in diabetic mice showed a significant reduction in blood glucose levels in fasted and fed conditions compared with AAV-null-treated mices or single treatment with AAV-mhIns or AAV-mhGcK.

The plasmids disclosed in the present invention, pAAV-MCS and pGG2, are for illustrative purposes only and are not intended, nor should they be interpreted, to limit the scope of the invention. Persons skill in the art can be used any plasmid known in the art capable of producing AAV by conventional methods known by persons skilled in the art (Sambrook et al., "Molecular cloning, a Laboratory Manual", 2nd ed., Cold Spring Harbor Laboratory Press, N.Y., 1989 Vol 1-3).

The impact of the gene transfer approach of present invention, consisting of co-expression of low levels of insulin together with the enzyme glucokinase in skeletal muscle, implies normalization of glycemia with a one-time intervention what results in a great improvement of patients' quality of life and prevention of severe and costly secondary complications of diabetes. It should be noted that, compared to other experimental therapeutic approach to diabetes, the gene therapy compositions and the method discloses in the present invention are based on engineering skeletal muscle, a readily accessible tissue that does not require any invasive procedure to be manipulated. This is a considerable advantage over other approaches disclosed in the state of the art, such as engineering the liver or transplanting insulin-producing β-cells. It should also be pointed out that the method disclosed in the present invention has the advantage of not requiring immunosuppression, as diabetic subjects are naturally immunologically tolerant to insulin and glucokinase; additionally, even basal (low) levels of expression of insulin and glucokinase may result in a dramatic improvement of the disease profile in terms of quality of life (better glycemic control) and reduction of insulin requirements. Thus, the use of two genes acting synergistically on glycemic control potentially represents a major advance in the management of T1D and T2D diabetes.

Furthermore, the present invention also disclosed that gene therapy with AAV-mhGcK could be combined with regular exogenous insulin injections to improve the conventional treatment of T1D. Additionally, AAV-GcK gene therapy per se could be considered as a treatment for diabetic patients in which insulin production is still present, such as in early phases of T2D development.

Therefore, the main embodiment of the invention corresponds to a gene therapy composition which comprises at least a first vector carrying and allowing the expression of insulin gene (Ins) and at least a second vector carrying and allowing the expression of glucokinase gene (Gck).

Further embodiments of the invention concern to gene therapy compositions wherein the first vector contains the CDS of SEQ ID NO. 1 or the CDS of SEQ ID NO. 3.

Other embodiments of the invention relate to gene therapy compositions, wherein the second vector contains the CDS of SEQ ID NO. 2 or the CDS of SEQ ID NO. 4.

More precisely, alternative embodiments of the invention consist in gene therapy compositions comprising either, a first vector containing the CDS of SEQ ID NO. 1 and a second vector containing the CDS of SEQ ID NO. 2; or a first vector containing the CDS of SEQ ID NO. 3 and a second vector containing the CDS of SEQ ID NO. 4.

In the gene therapy composition according to the invention, the first and the second vectors carrying genes can be the same, specifically that same vector can be a plasmid and more precisely a plasmid selected from: pGG2 (FIGS. 19 and 20) or pAAV (FIG. 5). Adeno-associated virus based vectors (AAV) are particularly preferred for working out present invention. Most preferred are the type 1 (AAV1).

The gene therapy compositions of the invention can be used in the treatment of diabetes in mammals, as a way of example, in dogs or pets in general and in human beings.

Also a last embodiment of the invention is to provide a method of treatment of diabetes in mammals, which comprise the administration to a subject in need of it, of a therapeutically effective dose of a gene therapy composition as mentioned above. Moreover, the gene therapy composition is administered, according to the method of invention, in a single and unique dose for all the treatment hence avoiding repeated periodical administration. More precisely, the single dose is administered to muscle tissue, accordingly to the method of invention, by means of an unique multi-needle injection.

Other embodiment of the invention relate to a mutated human insulin (mhIns) gene characterized by the CDS of SEQ ID NO: 3 and a mutated human glucokinase (mhGcK) gene characterized by the CDS of SEQ ID NO: 4. Also the invention relate the mutated human insulin (mhIns) and the mutated human glucokinase (mhGcK) genes, as disclosed previously, for the treatment of diabetes.

Present invention also disclosed a method of treatment of diabetes which comprises the administration to a subject in need of it, of a therapeutically effective dose of a gene therapy composition according to the present invention.

Moreover, the gene therapy composition disclosed herein, is administered in a single dose for all the treatment, to the muscle tissue by means of an unique multi-needle injection.

Other embodiment of the invention relate to a method of treatment of diabetes which comprises the administration to a subject in need of it, of a therapeutically effective dose of a gene therapy composition which comprises at least a vector carrying and allowing the expression of glucokinase gene (Gck). Moreover, the vector is an adeno-associated virus based vector that contains the CDS of SEQ ID NO: 2 or the CDS of SEQ ID NO: 4. More preferably, the method disclosed herein is the plasmid pAAV. Furthermore, the gene therapy composition used in the present method is administered in a single dose for all the treatment, to muscle tissue by means of an unique multi-needle injection. The present method further comprises exogenous insulin injections.

Unless defined otherwise, all technical and scientific terms used herein have the same meaning as commonly understood by one of ordinary skill in the art to which this invention belongs. However, for ease of reference, some of these terms will now be defined.

The term "mutated genes" refers to the introduction of mutations in the coding sequence of the genes with the purpose of increasing protein production. The criteria used for these mutations are exposed in Example 2.

The term "AAV-null-treated mice" as used throughout the present specification is to be understood to mean an adeno-associated virus (AAV)-based vector capsid and genome but without expression of any coding sequence.

FIGURE LEGENDS

FIG. 1. Efficient transduction and secretion of insulin from dog skeletal muscle. (A) Unique 5 needle injection system used to inject dog muscle. (B) AAV1-GFP can efficiently transduce large numbers of dog muscle fibres. (C) Human insulin was detected by Northern blot from autopsy samples in Dog 1, but not in uninjected control (Con) muscle.

Figure 2:
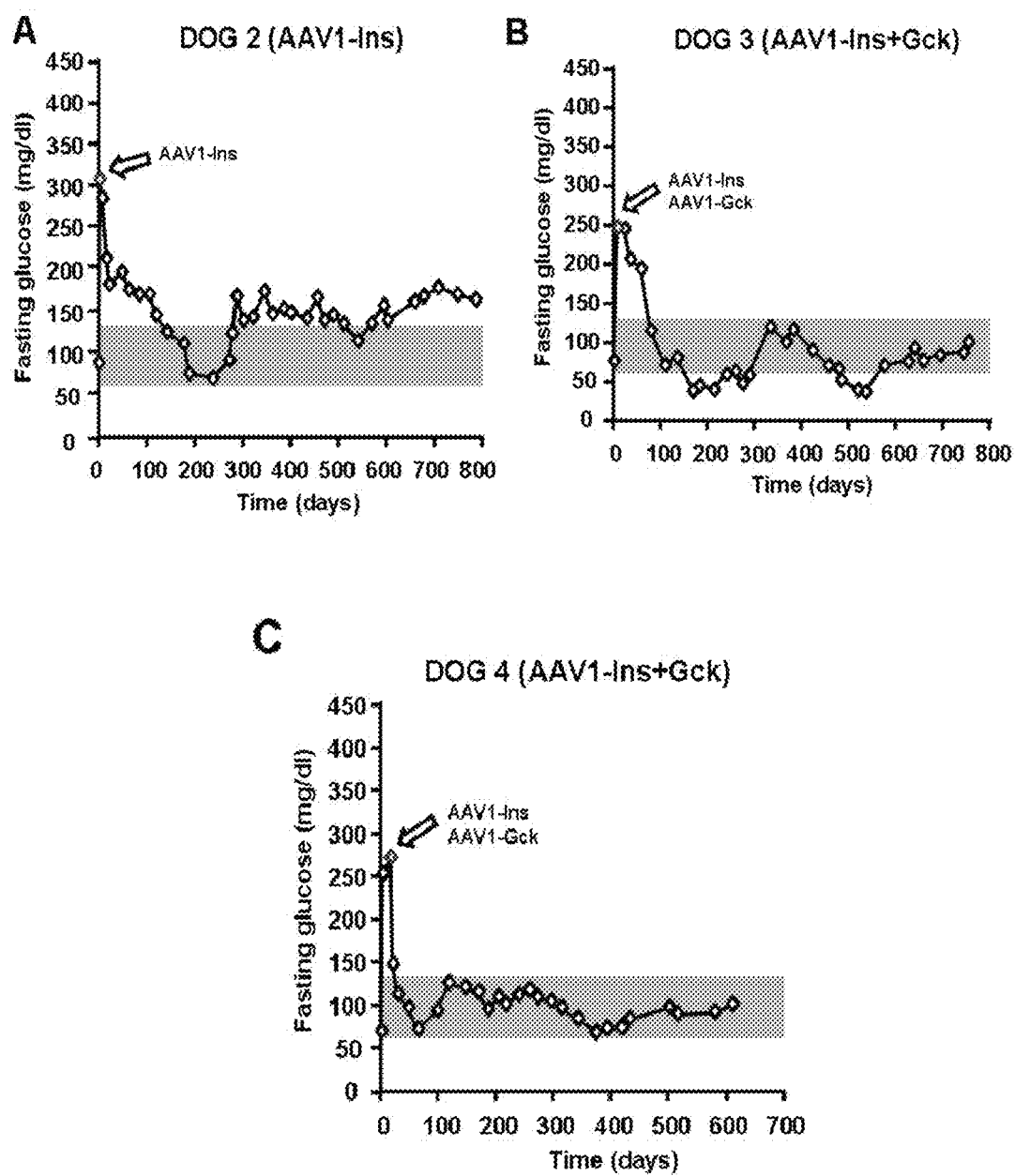

FIG. 2. Fasting glycemia profiles. (A) Dog 2 treated with $1.0 \times 10^{12}$ vg (vector genomes)/kg AAV1-humanIns. (B) Dog 3 and 4 treated with $1.0 \times 10^{12}$ vg/kg AAV1-humanIns and $1.0 \times 10^{12}$ vg/kg AAV1-ratGck. Arrows indicate AAV injection. Time after diabetes induction is shown and grey bars indicate range of normoglycemia.

Figure 3:
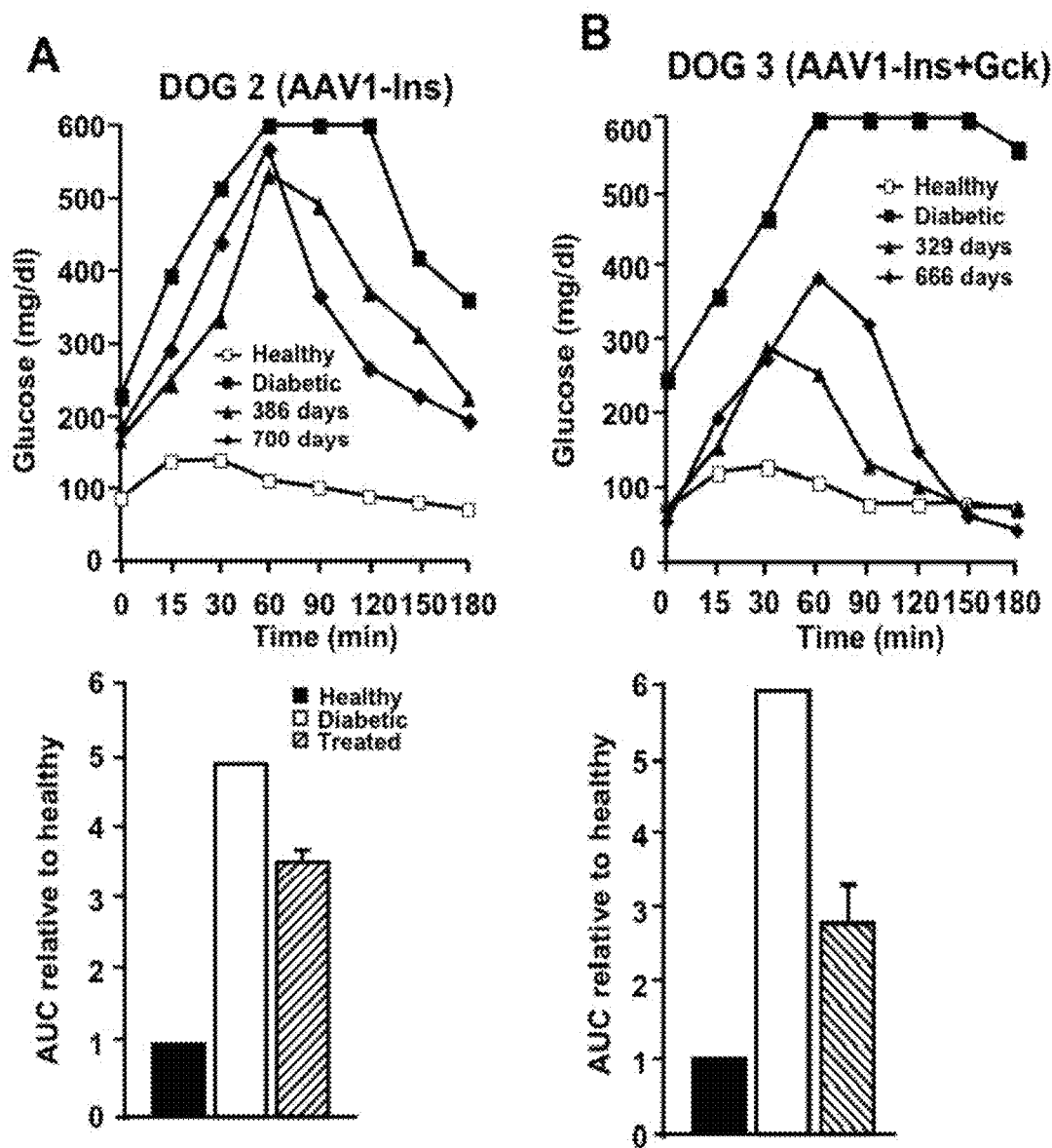
Figure 3:
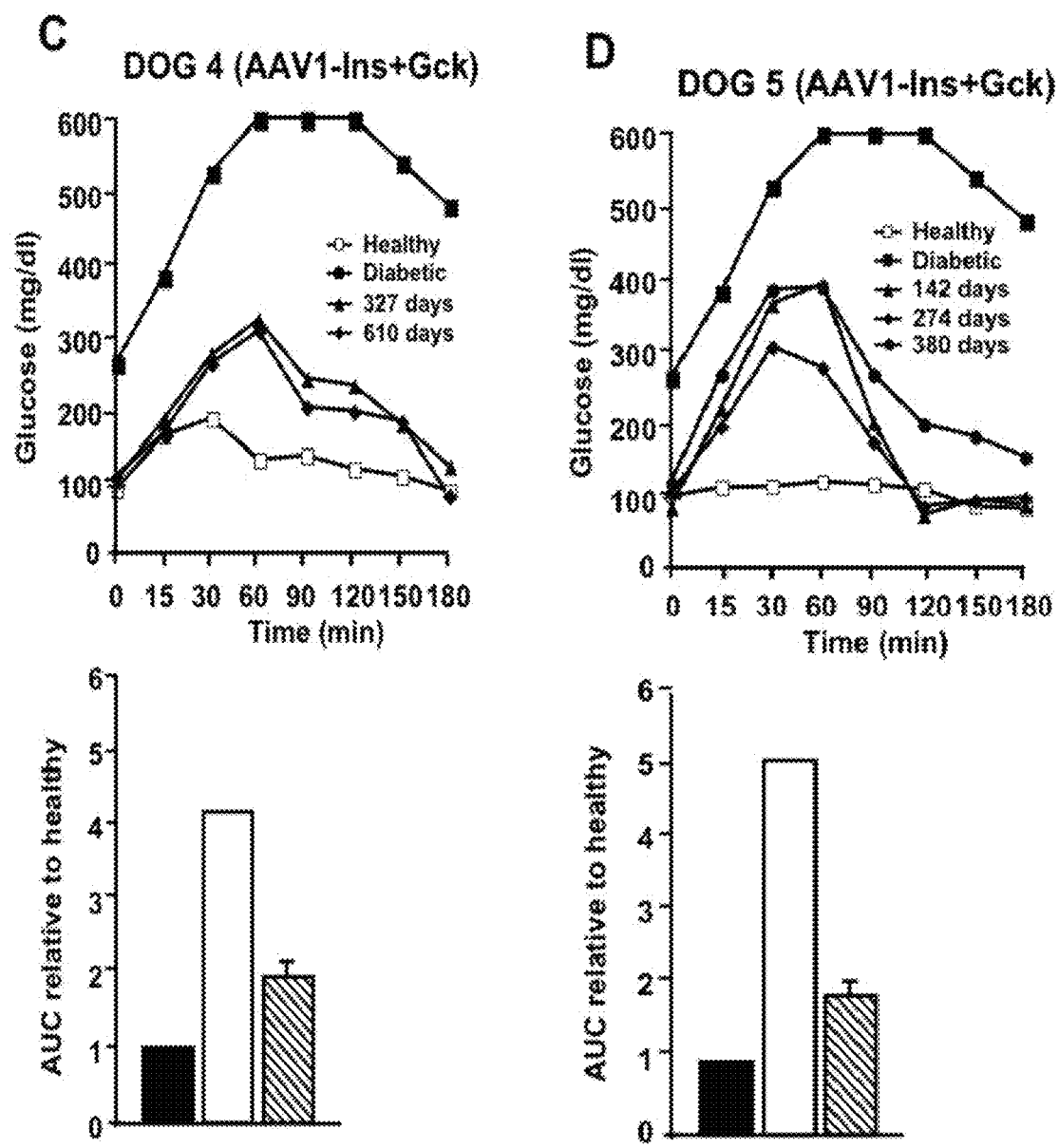

FIG. 3. Improved glucose disposal after oral glucose tolerance test (GTT) in dogs treated with AAV1-hIns+rGck. GTT was performed in the same dog before, after diabetes induction and at several time points after and AAV1-humanIns+ratGck treatment. Upper panel: GTT representative curves when healthy, diabetic non-treated and diabetic AAV-treated are shown; Lower panel: area under the curve. In the AAV-treated dogs, results are means+SEM of eight GTT. (A) Dog 2 showed no significant improvement to glucose disposal after treatment. (B) Dog 3 and (C) Dog 4 demonstrated improved ability to dispose of glucose during GTT. (D) Dog 5 after AAV1-humanIns+ratGck treatment showed a GTT profile similar to Dogs 3 and 4.

Figure 4:
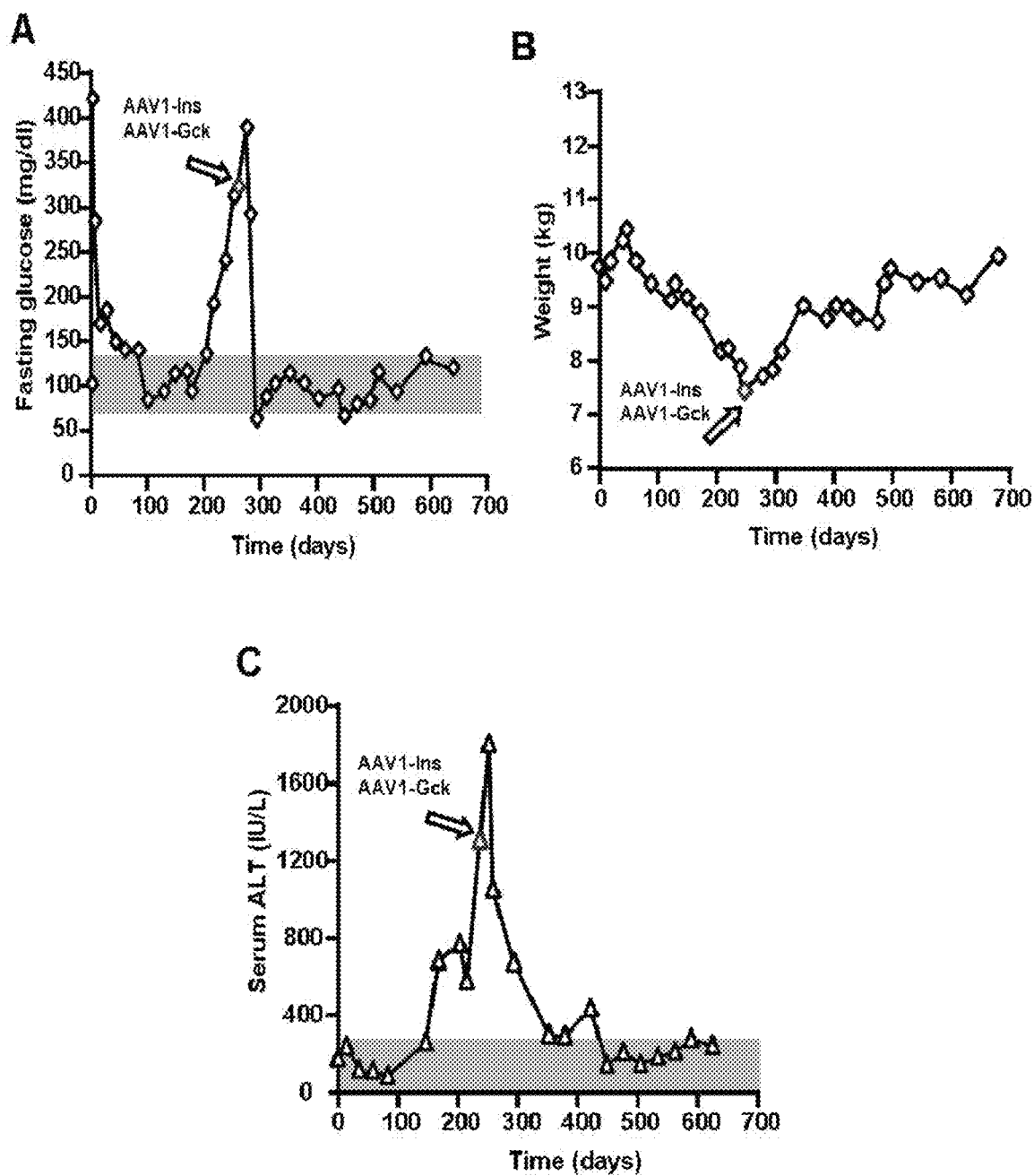

FIG. 4. Fasting glycemia profile, body weight and serum transaminase profile of Dog 5. (A) Dog 5 diabetic was treated with $1.0 \times 10^{12}$ vg/kg AAV1-humanIns and $1.0 \times 10^{12}$ vg/kg AAV1-ratGck. (B) Body weight profile. (C) Serum profile of alanine transaminase (ALT) activity. Arrows indicate AAV injection. Time after diabetes induction is shown and grey bars indicate range of normoglycemia (A) and normal ALT activity (C).

FIG. 5. Plasmid pAAV-MCS (Stratagene, Cedar Creek, Tex., USA). This plasmid contain the CMV promoter (pCMV) and polyA signal from growth hormone (hGHpA) flanked by the two Inverted Terminal Repeats (ITR) of AAV2.

Figure 6:
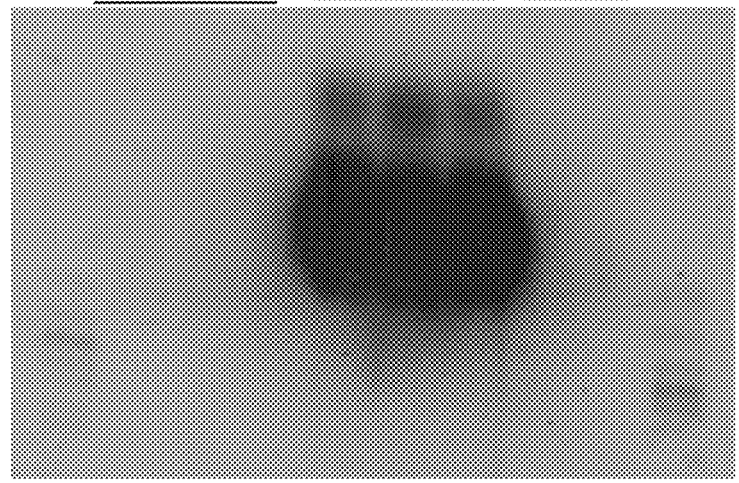
Figure 6:
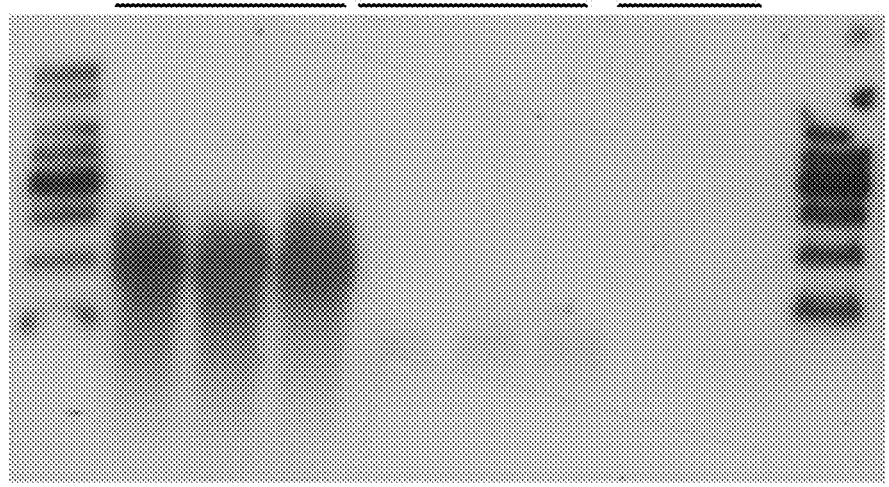

FIG. 6. Quantification of mRNA by Northern Blot in HEK293 cells transfected with pAAVmhINS and pAAVmhGK plasmids. pAAVmhINS is a plasmid that express mutated human insulin (mhINS) under the control of CMV promoter and contain ITR sequences from AAV2. pAAVmhGcK is a plasmid that express mutated human Glucokinase (mhGK) under the control of CMV promoter and contain ITR sequences from AAV2. HEK293 cells were transfected with the appropriate plasmid and total RNA was isolated 48 h after transfection. Northern Blot was performed with 10 ug of RNA and hibridized with the mhINS and the mhGck cDNA, respectively. Remarkable mhINS (a) and mhGck (b) expression was detected.

Figure 7:
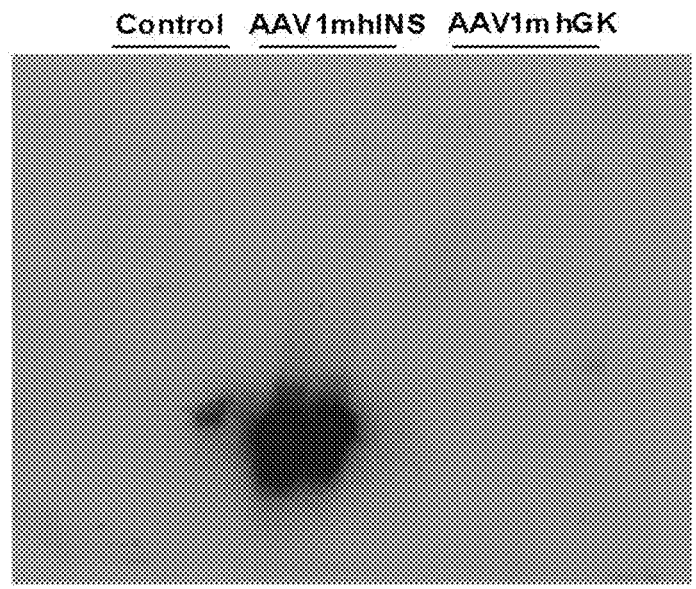
Figure 7:
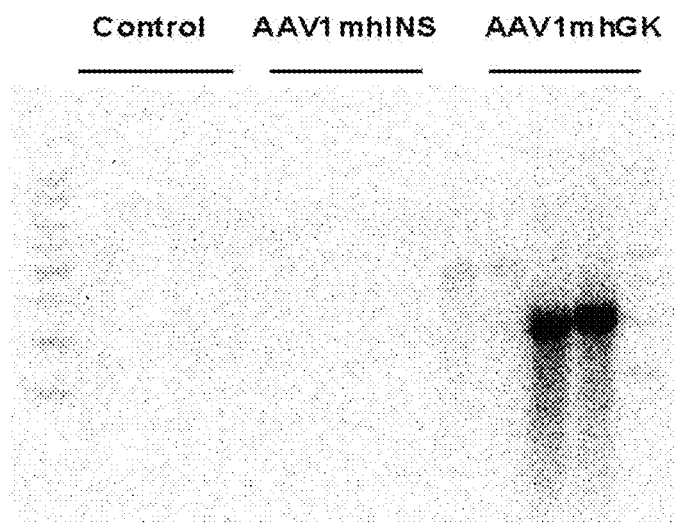

FIG. 7. Quantification of mRNA by Northern Blot in HEK293 cells transduced with AAV1-mhINS and AAV1-mhGK plasmids. AAV1 vectors were generated by triple transfection following standard methods using pAAVmhINS and pAAVmhGK plasmids as viral backbone. HEK293 cells were transduced with AAV1-mhINS or AAV1-mhGK and total RNA was isolated 48 h after transection. Northern Blot was performed with 10 ug of RNA and hibridized with the mhINS and the mhGck cDNA, respectively. Remarkable mhINS (a) and mhGck (b) expression was detected.

Figure 8:
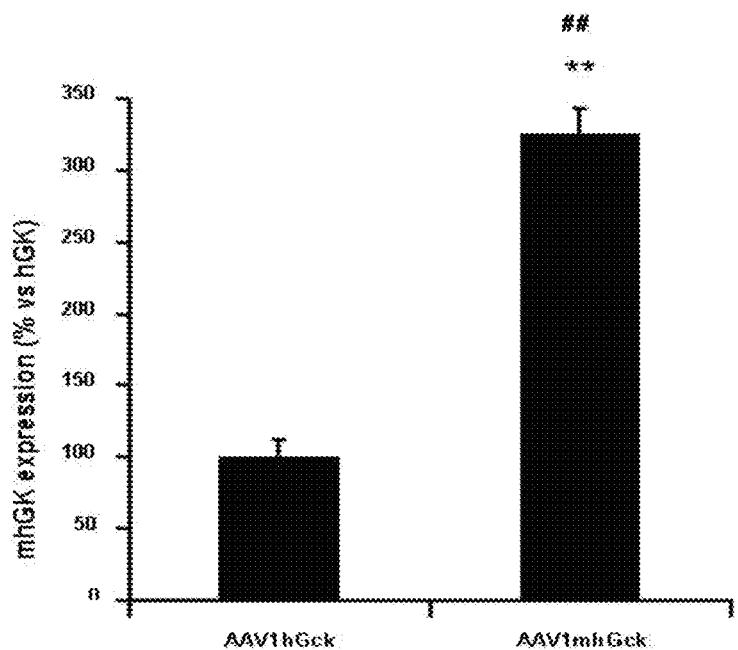

FIG. 8. Glucokinase protein levels measured by western blot analysis. (A) Densitometric analysis of Gck protein in westerns blots (n=3 per group) of GcK protein of HEK293 cells transduced with AAV1-rGck, AAV1-hGck and AAV1-mhGck. Values are represented as % of protein vs rGck vector. (B) Densitometric analysis of Gck protein in westerns blots (n=3 per group) of GcK protein of HEK293 cells transduced with AAV1-rGck, AAV1-hGck and AAV1-mhGck. Values are represented as % of protein vs hGck. ## $p<0.01$ vs hGck, ** $p<0.01$ vs rGck.

Figure 9:
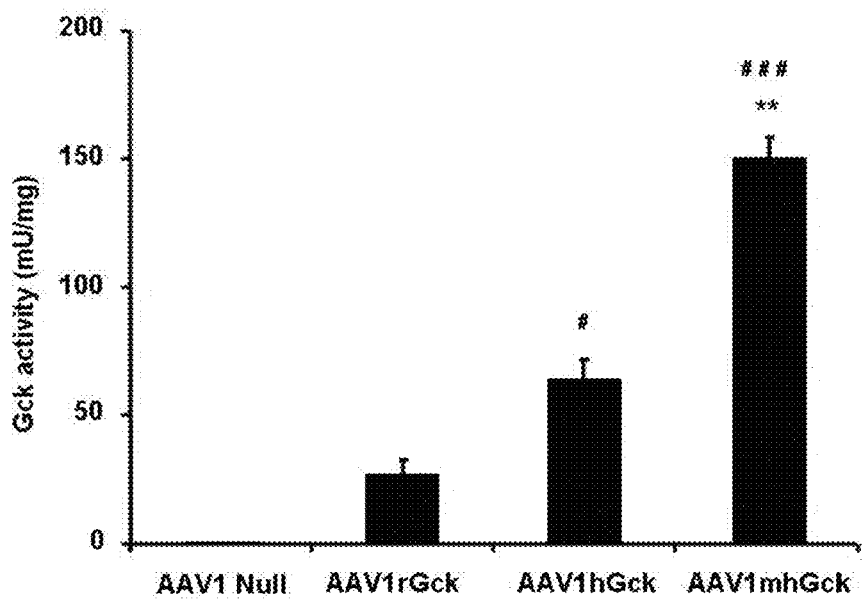

FIG. 9. Glucokinase activity in vitro. HEK293 cells were transduced with AAV1 null, AAV1-rGck, AAV1-hGck or AAV1-mhGck at a MOI=10E5 vg/cell. Glucokinase activity was measured in cell extracts and values are represented as μU/mg total protein (n=3 per group). ** $p<0.01$ vs hGck; # $p<0.05$ vs rGck; ### $p<0.001$ vs rGck.

Figure 10:
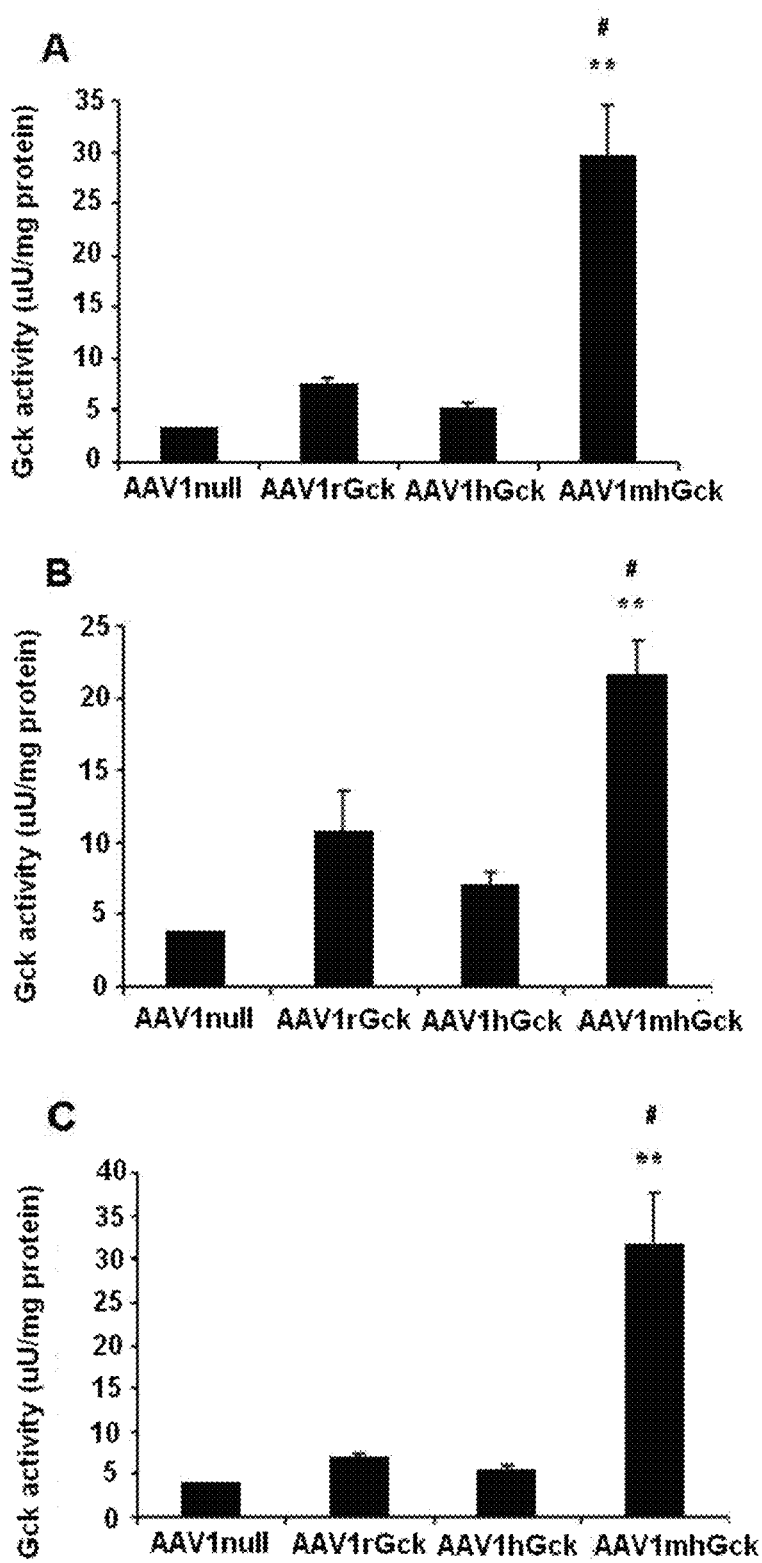

FIG. 10. Glucokinase activity in vivo. CD-1 healthy mice were injected in both hindlimbs: (A) quadriceps, (B) gastrocnemius and (C) tibialis, with AAV1null, AAV1-rGck, AAV1-hGck or AAV1-mhGck (10E12 vg/kg). Glucokinase activity was measured in skeletal muscle extracts and values are represented as μU/mg total protein (n=5 per group). # $p<0.05$ vs rGck; ** $p<0.01$ vs hGck.

Figure 11:
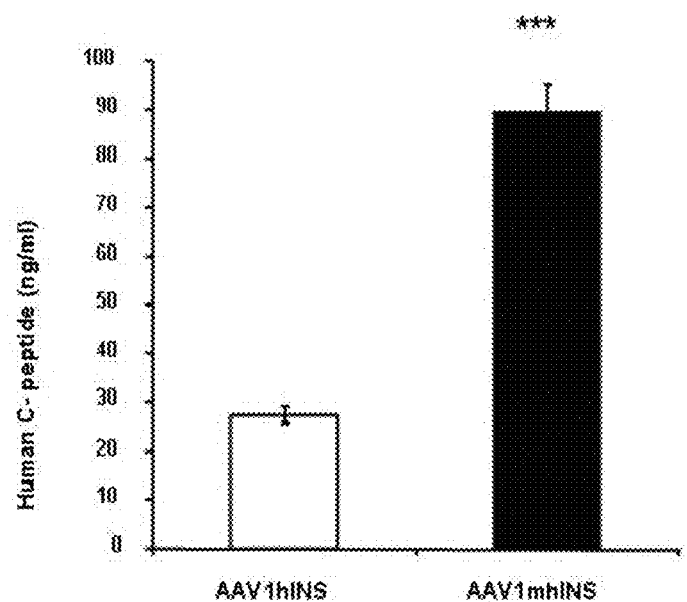
Figure 12:
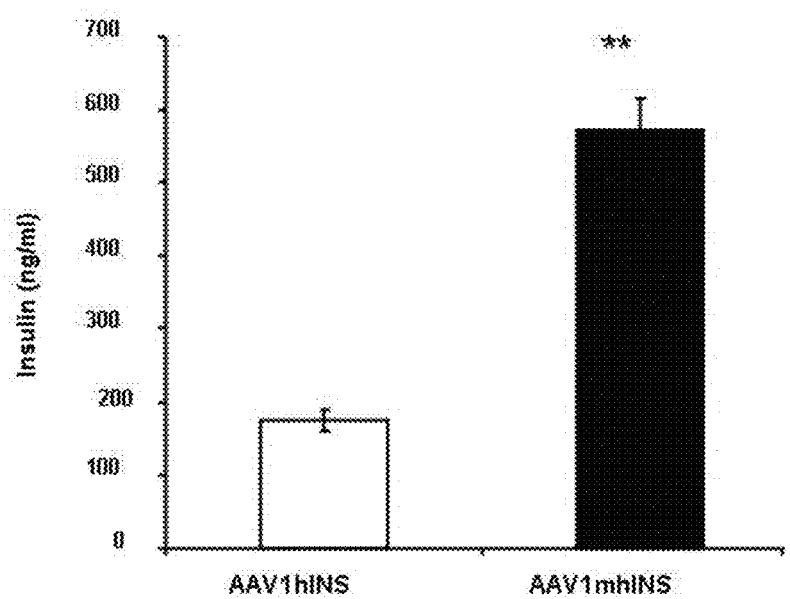

FIG. 11. Human C-peptide levels in culture media after HEK293 cells transduction with AAV1 vectors coding for mutated human insulin and non-mutated human insulin HEK293 cells were transduced at different MOI with adeno-associated vectors (AAV1) coding for the transgenes. Human C-peptide measured by RIA in culture medium 72 h after viral transduction. Significative increase in human C-peptide levels is observed in mutated insulin versus non-mutated insulin at MOI of 10E5 vg/cell. *** $p<0.001$ vs hINS FIG. 12. Insulin levels in culture media after HEK293 cells transduction with AAV1 vectors coding for mutated human insulin and non-mutated human insulin HEK293 cells were transduced at different MOI with adenoassociated vectors (AAV1) coding for the transgenes. Insulin was measured by RIA in culture medium 72 h after viral transduction. Significative increase in human insulin levels was observed in mutated insulin versus non-mutated insulin vectors at MOI of 10E5 vector genomes/cell. *p<0.01 hINS FIG. 13. Blood glycemia in mice treated with AAV1 vectors coding for mutated human insulin and non-mutated human insulin C57bl6 healthy mice were injected with AAV1-hINS or AAV1-mhINS in both hindlimbs (quadriceps, gastrocnemius and tibialis) at a dose of 1,4E11 vg/mouse. Fed glycemia was measured two weeks after viral injection (n=3 per group). * p<0.05 vs hINS.

Figure 14:
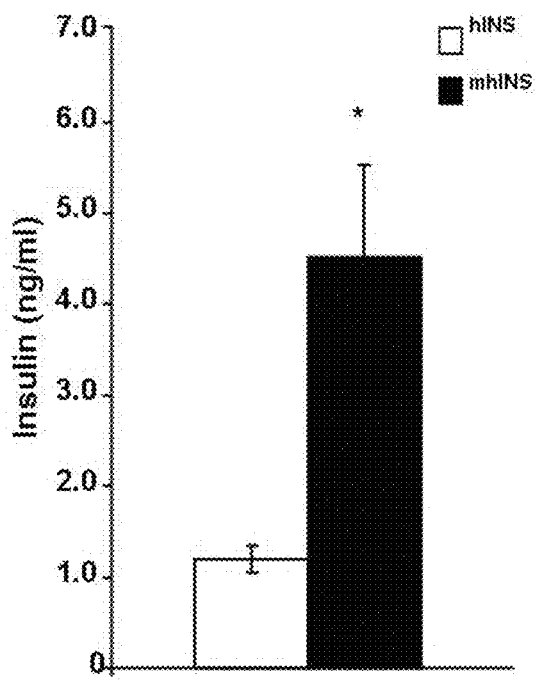
Figure 14:
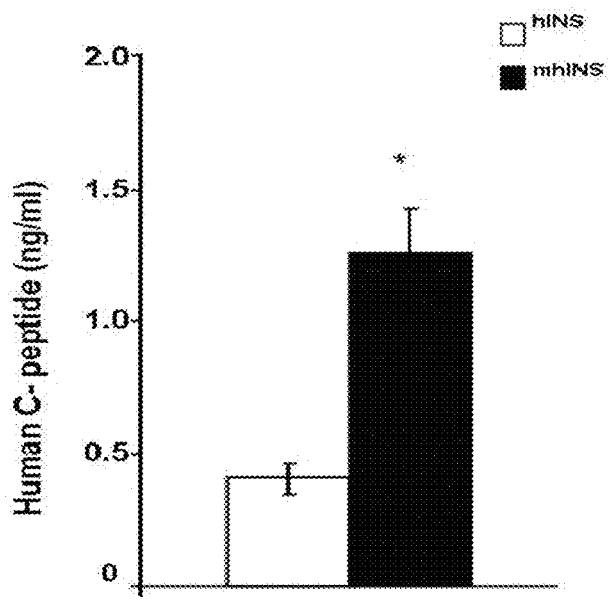

FIG. 14. Circulating levels of Human insulin and human C-peptide in mice treated with AAV1 vectors coding for mutated human insulin and non-mutated human insulin C57bl6 healthy mice were injected with AAV1-hINS or AAV1-mhINS in both hindlimbs (quadriceps, gastrocnemius and tibialis) at a dose of 1,4E11 vg/mouse and human insulin (A) and human C-peptide (B) were measured by RIA in serum two weeks after viral transduction. * p<0.05 vs hINS.

Figure 15:
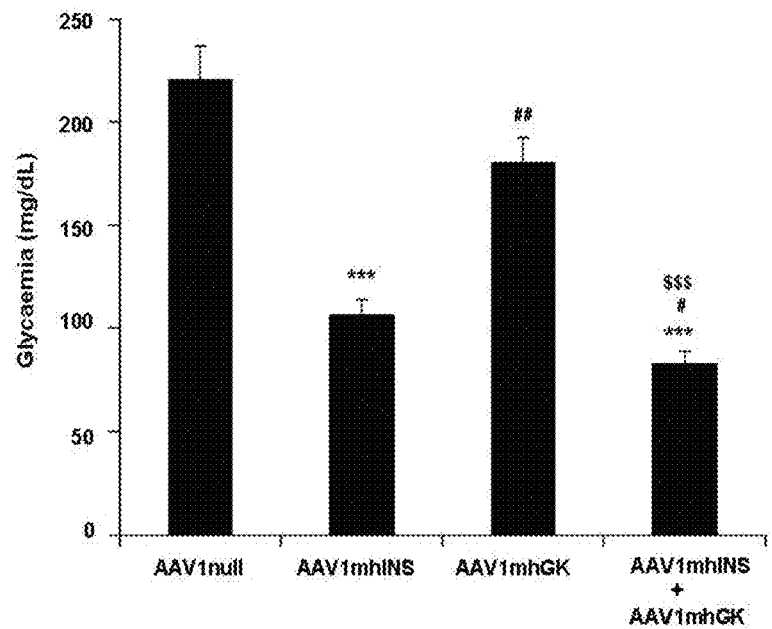

FIG. 15. Fasted blood glycemia in mice treated with AAV1 vectors coding for mutated human insulin and Gck. C57bl6 healthy mice were injected with AAV1-mhINS, AAV1-mhGck or both vectors in hindlimbs (quadriceps, gastrocnemius and tibialis) at a dose of 10E12 vg/kg. Fasted glycemia was measured one month after viral injection (n=20 per group). *** p<0.001 vs AAV1null; # p<0.05 vs mhINS; ## p<0.01 vs mhINS; $ $ $ p<0.001 vs mhGcK.

Figure 16:
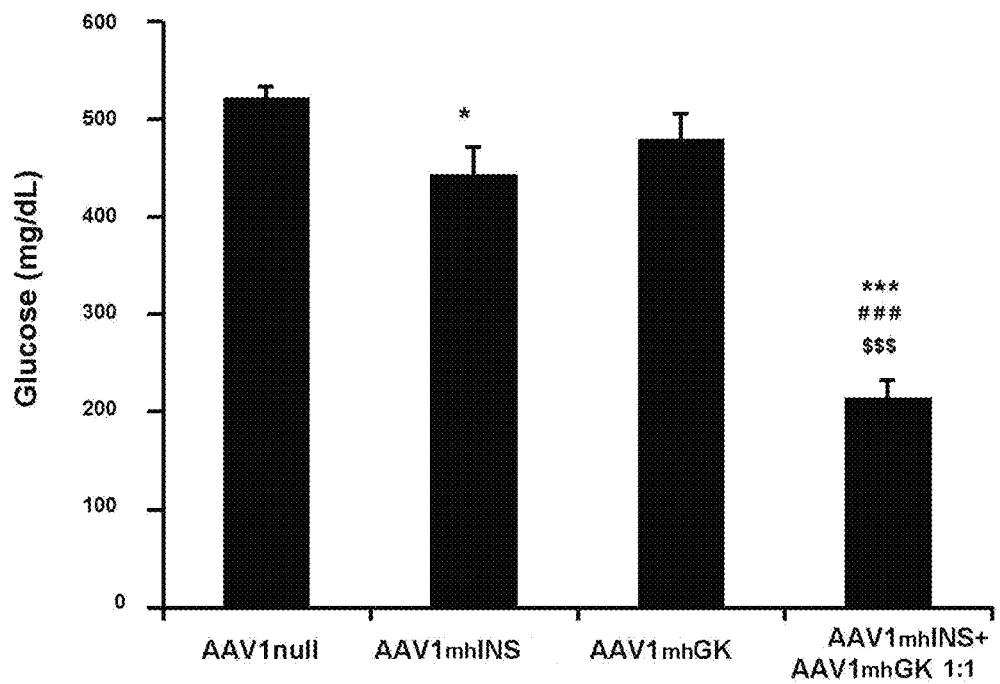

FIG. 16. Fed blood glycemia in mice treated with AAV1 vectors coding for mutated human insulin and Gck. C57bl6 healthy mice were injected with AAV1-mhINS, AAV1-mhGck or both vectors in hindlimbs (quadriceps, gastrocnemius and tibialis) at a dose of 10E12 vg/kg. Fed glycemia was measured one month after viral injection (n=20 per group). *** p<0.001 vs AAV1null; # p<0.05 vs mhINS; $$$ p<0.001 vs mhGK.

Figure 17:
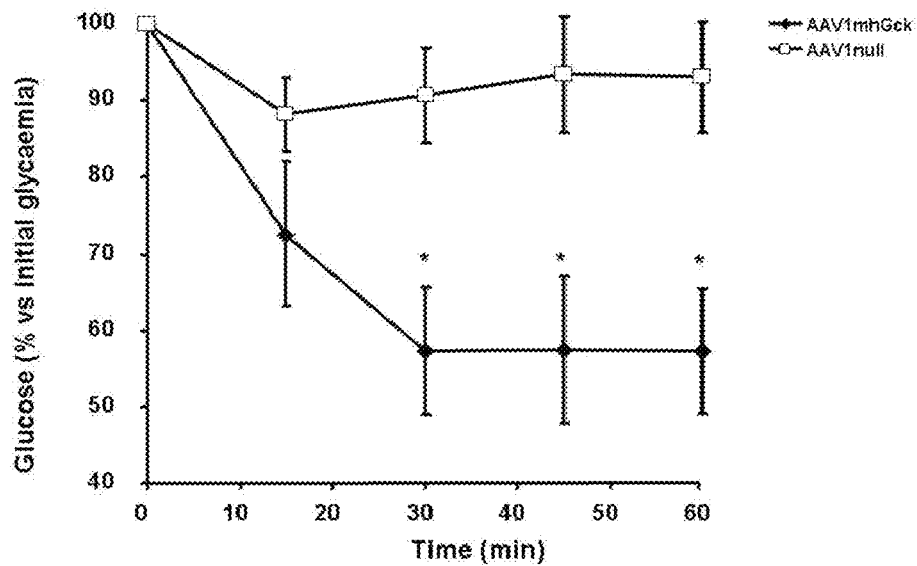

FIG. 17. Insulin tolerance test in T1D animals treated with AAV1-mhGcK. Experimental diabetes was induced in 2 month-old c57bl6 mice by 5 daily consecutive dosis of STZ (50 mg/kg). Two weeks after STZ, AAV1-mhGck or AAV1-null vectors were injected into the hindlimbs at a dose of 10E12 vg/kg. One month after viral administration an intraperitoneal insulin tolerance test was performed (0.375 U/kg) (n=7 per group). * p<0.05 vs null.

Figure 18:
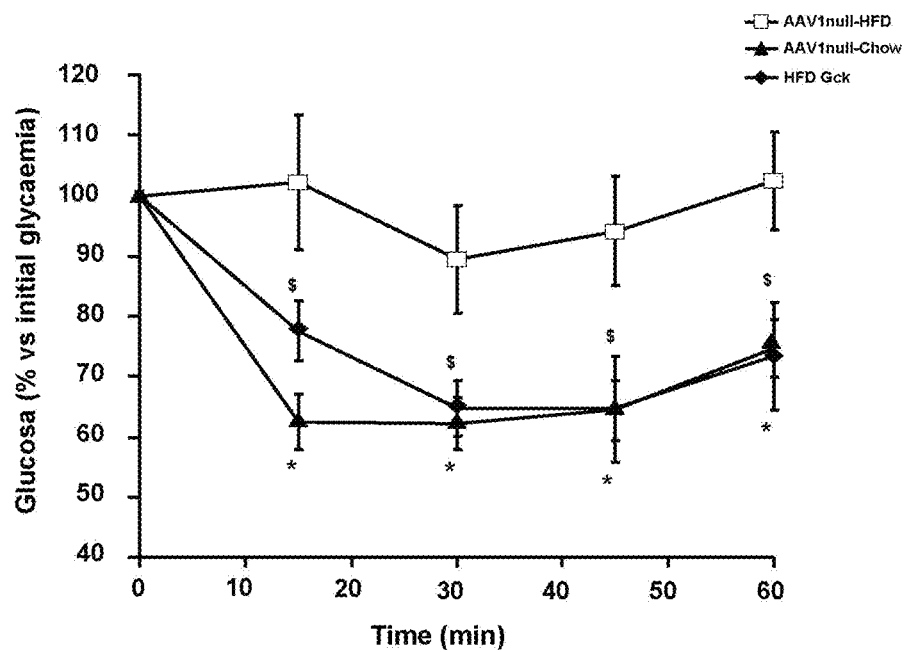

FIG. 18. Insulin tolerance test in T2D animals treated with AAV1-rGcK. AAV1-rGck or AAV1-null (control) vectors were injected into the hindlimbs of 2 month-old c57bl6 mice at a dose of 10E12 vg/kg. Three months after viral administration an intraperitoneal insulin tolerance test was performed (0.75 U/kg) (n=10 per group). $ p<0.05 high fat diet (HFD) Gck vs AAV1null-HFD; * p<0.05 Control-Chow vs AAV1 null-HFD.

FIG. 19. Plasmid pGG2-rGK. This plasmid contain the CMV promoter, the CDS of the rat Gck and polyA signal from SV40 flanked by the two Inverted Terminal Repeats (ITR) of AAV2.

FIG. 20. Plasmid pGG2-Ins. This plasmid contain the CMV promoter, the CDS of the human INS gene and polyA signal from SV40 flanked by the two Inverted Terminal Repeats (ITR) of AAV2.

DETAILED DESCRIPTION OF THE INVENTION

The significance and potential impact of the gene therapy invention approach, consisting of co-expression of low levels of insulin together with the enzyme glucokinase in skeletal muscle, are potentially enormous. Normalization of glycemia with a one-time intervention would result in a great improvement of patients' quality of life and prevention of severe and costly secondary complications of diabetes. The data disclosed in the present invention show that this is feasible and safe. It should be noted that, compared to other experimental therapeutic approach to diabetes, the strategy displayed in the invention is based on engineering skeletal muscle, a readily accessible tissue that do not require any invasive procedures to be manipulated. This is a considerable advantage over other approaches, such as engineering the liver or transplanting insulin-producing β-cells. It should also be pointed out that the gene therapy composition and the method disclosed herein have the advantage of not requiring immunosuppression, as diabetic subjects are naturally immunologically tolerant to insulin and glucokinase; additionally, even basal (low) levels of expression of insulin and glucokinase may result in a dramatic improvement of the disease profile in terms of quality of life (better glycemic control) and reduction of insulin requirements. Thus, the use of two genes acting synergistically on glycemic control potentially represents a major advance in the management of T1D and T2D diabetes worldwide.

Therefore, the present invention relates gene therapy compositions which comprise at least a first vector carrying and allowing the expression of insulin gene (Ins) and at least a second vector carrying and allowing the expression of glucokinase gene (Gck). As alternative, the gene therapy compositions of present invention comprise a single vectors carrying and allowing the expression of both genes (Ins and GcK) operatively linked. Moreover, Ins and/or GcK genes can be, any of them independently, autologous or heterologous genes with regard to the species wherein are being expressed.

In a particular embodiment of the gene therapy compositions of the invention are characterized by the vectors are adeno associated virus based vector.

In another particular embodiment of the gene therapy composition disclosed in the present invention, the first vector contains the CDS of SEQ ID NO. 1 or the CDS of SEQ ID NO. 3.

In another particular embodiment of the gene therapy composition disclosed in the present invention, the second vector contains the CDS of SEQ ID NO. 2 or the CDS of SEQ ID NO. 4.

In another particular embodiment of the gene therapy composition, the first and the second carrying gene vectors are the same.

In another particular embodiment of the gene therapy composition, comprises a first vector containing the CDS of SEQ ID NO. 1 and a second vector containing the CDS of SEQ ID NO. 2.

In another particular embodiment of the gene therapy composition disclosed herein, the first vector is AAV-Ins and the second vector is AAV-GcK.

In another particular embodiment, the gene therapy composition of the invention comprises a first vector containing the CDS of SEQ ID NO. 3 and a second vector containing the CDS of SEQ ID NO. 4.

In another particular embodiment of the gene therapy composition disclosed in the present invention, the first vector is AAV-mhIns and the second vector is AAV-mhGcK.

In another particular embodiment, the gene therapy composition of the invention comprises a first vector containing the CDS of SEQ ID NO. 1 or the CDS of SEQ ID NO: 3 and a second vector containing the CDS of SEQ ID NO. 2 or the CDS of SEQ ID NO: 4.

In another particular embodiment, the gene therapy composition of the invention is characterized by the first vector is selected from AAV-Ins or AAV-mhIns and the second vector is selected from AAV-GcK or AAV-mhGcK.

Present invention also relates gene therapy compositions for use in the treatment of diabetes in mammals.

In a particular embodiment of the gene therapy compositions disclosed herein, the mammal is a rodent, preferably mice, rats, gerbils and guinea pigs and more preferably mice and rats.

In another preferred embodiment of the gene therapy compositions disclosed herein, the mammal is a dog.

In another preferred embodiment of the gene therapy compositions disclosed herein, the mammal is a human being.

Present invention also disclosed a mutated human insulin (mhIns) gene characterized by comprising the CDS having SEQ ID NO: 3 and a mutated human glucokinase (mhGcK) gene characterized by comprising the CDS having SEQ ID NO: 4.

Another object disclosed in the present invention is the mutated human insulin (mhIns) gene, as disclosed previously, for use in the treatment of diabetes.

Present invention also disclosed the use of the mutated human insulin (mhIns) gene disclosed herein for the manufacture of a medicament and/or a gene therapy composition for use in the treatment of diabetes.

Another object disclosed in the present invention is the mutated human glucokinase (mhGcK) gene, as disclosed previously, for use in the treatment of diabetes.

Present invention also disclosed the use of the mutated human glucokinase (mhGcK) gene disclosed herein for the manufacture of a medicament and/or a gene therapy composition for use in the treatment of diabetes.

Present invention also disclosed a method of treatment of diabetes which comprises the administration to a subject in need of it, of a therapeutically effective dose of a gene therapy composition according to the present invention.

In a preferred embodiment of the invention, the method comprises the administration of the gene therapy composition disclosed herein, in a single dose for all the treatment.

In another preferred embodiment of the invention, the method disclosed that the single dose is administered to muscle tissue by means of an unique multi-needle injection.

Present invention also disclosed a method of treatment of diabetes which comprises the administration to a subject in need of it, of a therapeutically effective dose of a gene therapy composition which comprises at least a vector carrying and allowing the expression of glucokinase gene (Gck).

In a preferred embodiment of the method of the present invention, the vector is an adeno-associated virus based vector.

In another preferred embodiment of the method disclosed herein, the vector comprises the CDS having either SEQ ID NO: 2 or SEQ ID NO: 4.

In another preferred embodiment of the method disclosed herein, the vector is selected from AAV-mhGcK or AAV-GcK.

In another preferred embodiment of the method disclosed herein, the gene therapy composition is administered in a single dose for all the treatment.

In another preferred embodiment of the method disclosed herein, the single dose is administered to muscle tissue by means of an unique multi-needle injection.

In another preferred embodiment of the invention the method further comprises exogenous insulin injections.

The invention will now be described in more detail by way of examples. The following examples are for illustrative purposes only and are not intended, nor should they be interpreted, to limit the scope of the invention.

Example 1: Ins+Gck Gene Transfer to Skeletal Muscle in Diabetic Dogs

Studies in diabetic Beagle dogs used a unique 5-point needle (FIG. 1A) to obtain widespread expression of a GFP reporter in skeletal muscle (FIG. 1B). Subsequently, 2.5× $10^{12}$ vg/kg of AAV1-human Ins was injected into Dog 1 three days after diabetes induction with streptozotocin+ alloxan (50). Low levels of circulating human C-peptide were observed 4 days later, peaking after 2 weeks in association with hypoglycemia. Dog 1 was sacrificed 21 days after treatment and strong insulin expression was detected in biopsies of the treated area (FIG. 1C). These results indicated that AAV vectors injected in multiple sites can efficiently deliver the insulin gene to widespread areas and that AAV-mediated gene transfer of insulin to a large animal model of diabetes was feasible, resulting in large amounts of insulin produced and secreted from the dog skeletal muscle.

Next goal of present invention was to determine the optimum dose able to achieve therapeutic efficacy without causing hypoglycemia. To this end, Dog 2 was injected with $1.0\times10^{12}$ vg/kg of AAV1-human Ins after diabetes induction. After gene transfer, fasting glycemia decreased to reach normoglycemia without becoming hypoglycemic (FIG. 2A). After ~300 days, the fasting glycemia values became slightly hyperglycemic and have since remained stable. However, even when normoglycemic, we did not see a significant improvement in the ability of this dog to dispose glucose (FIG. 2A). This was despite detecting human C-peptide ~70 days after treatment, with stable levels achieved after 130 days those have lasted for more than 800 days, suggesting the long-term potential of this treatment. Muscle biopsies taken 14 and 270 days after treatment showed detectable insulin RNA at both time points, whereas a pancreas biopsy at day 270 showed less than 10% residual β-cell mass and no sign of regeneration. Dog 2 demonstrated no adverse events, no signs of toxicity and had a normal weight gain profile suggesting that even modest levels of circulating insulin can have beneficial effects.

Dog 3 and Dog 4 were made diabetic and treated with the same dose of AAV1-human Ins as Dog 2 and an equal dose ($1.0\times10^{12}$ vg/kg) of AAV1-rat Gck. Both Dog 3 and 4 showed a more accelerated return to fasting normoglycemia (FIG. 2B). These dogs remained normoglycemic for a long period (>2 years). Circulating human insulin and C-peptide levels in these dogs were detectable after treatment and, importantly, both Dogs 3 and 4 showed an improved GTT profile compared with Dog 2 (FIG. 3B, C). Muscle biopsies 15 and 113 days after viral injection revealed strong expression of both insulin and Gck, whereas a pancreas biopsy at 113 days confirmed <5% residual β-cell mass. No muscle damage was seen and, like Dog 2, we observed normal weight gain and no toxicity. Together, these data suggests that the combined treatment with human Ins and rat Gck leads to more beneficial effects in terms of improvement of glycemic control; these effects were not observed in Dog 2 despite the expression of insulin.

Then experimental diabetes in Dog 5 was induced and followed long-term progression of diabetes. Despite the complete absence of exogenous insulin treatment, this dog showed a gradual return to fasted normoglycemia, also coinciding with summer times. About six months after diabetes induction, we observed a severe rise in glycemia (FIG. 4A) parallel with a strong decrease in body weight (>30%) and marked increase in liver transaminases (FIG. 4B, C). At that moment, Dog 5 was treated with the same doses of AAV1-Ins and AAV1-Gck as Dog 3 and 4, which resulted in dramatic improvements of its metabolic profile. Fasting glycemia dropped sharply within 30 days of treatment (FIG. 4A), coinciding with a rise in circulating human C-peptide and a persistent weight gain (FIG. 4B). Biochemical signs of liver damage also normalized (FIG. 4C) and, most importantly, we observed an improved glucose disposal by GTT reminiscent of Dog 3 and 4 (FIG. 3D).

These results clearly demonstrate the beneficial effects of combined Ins+Gck therapy in long-term diabetic dogs. Therefore, joint expression of insulin and Gck in skeletal muscle is a safe approach that allows long-term survival in large diabetic animals (>2 years), body weight maintenance, normal physical performance and normalization of serum parameters.

Example 2: Construction of Mutated Vectors for Efficient Expression of Human Insulin and Human Glucokinase The coding sequence of either human insulin gene (hIns), containing specific sites for furin processing (36), or human glucokinase gene (hGcK) was modified to obtain codon mutated sequences (mhIns or mhGcK, respectively) following GeneArt procedures (48). GeneArt process involves avoiding cis-acting sequence motifs as:
  Internal TATA-boxes, chi-sites and ribosomal entry sites
  AR-rich or GC-rich sequence stretches
  RNA instability motifs
  Repeat sequences and RNA secondary structures
  (Crytic) splice donor and acceptor sites in higher eukaryotes The codon usage was adapted in GeneArt process to codon bias of *Mus musculus* genes. In addition, regions of very high (>80%) or very low (<30%) GC content were avoided when possible. The mutated gene constructs obtained showed CAI (codon adaptation index) of 0.96 what means high and stable expression rates in *Mus musculus*. GC-content adjustment made by the process of GenArt, prolongs mRNA half-life of the mutated construct achieved. The mutated human insulin and GcK genes described herein are then called mutated human genes. The mutated insulin and GcK cDNA was cloned in the multicloning site of the pAAV-MCS plasmid (Stratagene; FIG. 5) resulting in the plasmids pAAV-mhIns and pAAV-mhGcK respectively. This plasmid contains the CMV promoter and polyA signal from growth hormone flanked by the two Inverted terminal repeats (ITR) of AAV2. ITR sequences are required for packaging of the AAV genome into the AAV capsid, and are required for replication of the AAV genome during AAV production. Adeno-associated vectors were generated by triple transfection of Human Embryonic Kidney 293 cells (HEK293) cells according to standard methods.

HEK293 are cells from human origin that are stable transfected with the adenovirus E1 gene. The adenovirus E1 gene is required for adenovirus replication and also acts as a helper gene for AAV replication. The invention uses HEK293 cells for several purposes:
  1.—AAV production using triple transfection method. For AAV production, it is required to have the cassette of expression flanked by ITR (plasmid 1), a plasmid coding for Rep and Cap genes from the AAV (plasmid 2; provides replication functions for AAV genome and the capsid proteins depending on the desired serotype), a third plasmid coding for the essential genes of adenovirus required to provide helper function and support replication of AAV (plasmid 3, also named as adenovirus helper plasmid with code for E2, E4 and VA genes). In addition to E2, E4 and VA, E1 gene is necessary for replication of AAV, in this case E1 gene is provided by the HEK293cells instead of being in the adenovirus helper plasmid.
  2.—For DNA transfection. The inventors have used HEK293 to study expression, processing and secretion of insulin and expression of GK because they are very efficiently transfected with plasmid using calcium phosphate method.
  3.—HEK293 cells were also used to study expression, processing and secretion of insulin and expression of GK from AAV1 vectors, because this cell line (and not others) are permissive for AAV1-transduction.

Cells were cultured in roller bottles (RB) (Corning, Lowell, Mass.) in DMEM 10% FBS to 80% confluence and co-transfected with a plasmid carrying the expression cassette flanked by the viral ITRs (described above), a helper plasmid carrying the AAV rep2 and cap1 genes, and a plasmid carrying the adenovirus helper functions (both plasmids kindly provided by K. A. High, Children's Hospital of Philadelphia). Vectors were purified with an optimized method based on two consecutives cesium chloride gradients (49), dialyzed against PBS, filtered, titred by qPCR and stored at −80° C. until use.

Example 3: 'In Vitro' Expression of mRNA from Mutated Transgenes

HEK293 cells were transfected with pAAVmhINS and pAAVmhGck using calcium phosphate standard method. For experiments using AAV vectors, HEK293 cells were infected with AAV1mhINS and AAV1mhGck at different MOI (i.e. 10E4, 10E5, 10E6 vg/cell). Two days after transfection, cells were lysated with 1 ml of Tripure (Roche) and total RNA was extracted with RNAEasy Mini Kit (Qiagen). A Northern Blot was performed with 10 ug of RNA and hibridized with the mhINS (CDS of SEQ ID NO: 3) or the mhGck (CDS of SEQ ID NO: 4) cDNA, respectively (FIG. 6). Since these plasmids showed a high expression level of the gene of interest, adenoassociated type 1 viral vectors carrying these constructs were produced. Subsequently, AAV vectors were tested for their mRNA expression in HEK293 cells 96 h after transduction. High levels of transgene expression were detected by Northern Blot both with AAV1-mhINS and AAV1-mhGcK (FIG. 7).

Example 4: 'In Vitro' Expression of mhGcK Protein from Mutated Trangenes

In addition to increased RNA expression, the present invention has also detected a substantial increase in mhGcK protein production by the mutated construct (FIG. 8). Codon mutated human Gck construct produce 600% more protein than the rat Gck construct and 300% more protein than the human Gck transgene (=non codon mutated). This data, together with data disclose in Example 3 (FIGS. 6 and 7) of the present invention demonstrate that mhGck construct result in higher RNA and protein production compare with construct carrying rGcK or the wild type human Gck gene.

To demonstrate functionality of these novel constructs, AAV1 vectors coding for rat Gck (rGcK, NM_012565), wild type human Gck (hGck, NM_033507) or codon mutated human Gck (mhGck, CDS of SEQ ID NO: 4) were produced as disclosed in the previous Example 3 and 4. HEK293 cells were transduced with the 3 different vectors and Gck activity was measured. As shown in FIG. 9, the Gck activity of codon mutated (mhGcK) construct was higher than wild type human (hGcK) construct and rat Gck (rGcK) construct.

Example 5: 'In Vivo' Expression of GcK Protein from Mutated Trangenes

To provide in vivo evidences of Gck function, the inventors injected AAV1 vectors coding for rGck, hGck and mhGck into 3 different muscles in the hindlimbs of healthy mice. One month after the injection these muscles were harvested and analyzed for Gck activity. As shown in FIG. 10, muscles treated with mhGck vectors disclosed higher Gck activity compare with hGck and rGck.

These results clearly demonstrated superior effect of AAV1-mhGck vectors vs AAV1-rGck or AAV1-hGck and suggested that lower doses of codon mutated insulin vectors will be required to achieve same therapeutic effect than non-mutated vectors.

Example 6: Mutated Construct Showed an In Vitro and In Vivo Increased Insulin and C-Peptide Production Compare to Standard Vectors We aimed to compare the ability of the mutated insulin gene versus the non mutated insulin gene to produce human c-peptide and human insulin production. To this end, we transduced HEK293 cells with two different adenoassociated vectors (AAV1mhINS) at 3 different MOIs (10E4, 10E5 and 10E6 vg/cell). Four wells per MOI and vector were used. Two days after the infection, standard culture media (DMEM+10% FBS) was changed to a serum-free media to avoid the RIA detection of the media containing insulin. Next day (three days after the infection) medium was collected and was analyzed by RIA for the human C-peptide and insulin quantification.

Then it was observed a significant increase in human C-peptide levels (FIG. 11) and human insulin levels (FIG. 12) in AAV1-mhINS treated cells compared with standard insulin construct (AAV1-hINS). These data demonstrate that mutated insulin construct is more efficient in protein production and secretion that standard insulin gene.

Figure 13:
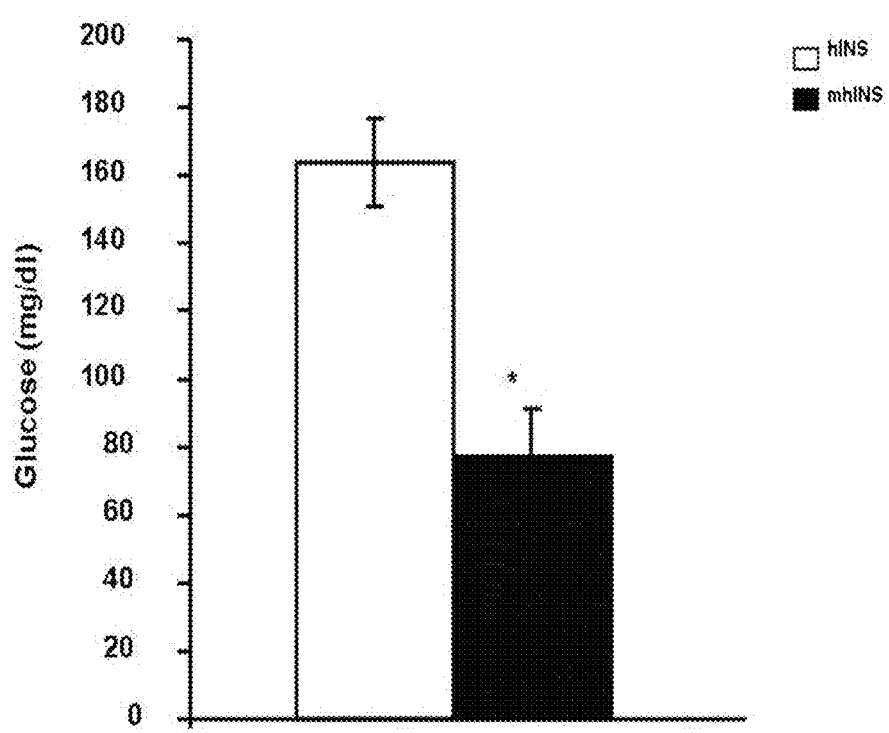

To provide in vivo evidences of increased insulin and C-peptide production between AAV1-mhINS vs AAV1-hINS vectors, healthy mice were injected in hindlimb muscles with a total dose of 1,4E11 vg/mouse. Glycemia and insulinemia was measured two weeks after viral injection. As shown in FIG. 13, a significant reduction in fed glycemia was observed in animals injected with AAV1-mhINS compare with AAV1-hINS. In agreement with this, insulinemia (FIG. 14A) and c-peptide (FIG. 14B) was higher in AAV1-mhINS treated mice.

The data disclosed in the present invention, clearly demonstrated a superior effect of AAV1-mhINS vectors vs AAV1-hINS and suggested that lower doses of codon mutated insulin vectors will be required to achieve same therapeutic effect than non-mutated vectors (hINS).

The use of lower doses of vectors may have several advantages for gene therapy:
a) potential immunological responses might be reduced since it has been suggested that immunological responses to AAV are dose dependent,
b) lower number of injection sites to distribute the insulin vector will be required.
c) vector manufacture demand will be lower.

Example 7: Combined Therapy AAV1-mhINS+AAV1-mhGck

The present invention tested the efficacy of a combined gene therapy approach with AAV1 vectors carrying codon mutated human constructs in diabetic mice. To this end, we injected AAV1-mhGcK vectors, AAV1-mhINS or both (10E12 vg per vector/kg) into the hindlimbs of c57b16 diabetic mice. Experimental T1D was induced by streptozotocin (STZ) administration as in (36) and viral vectors were injected 15 days after STZ. A control group of STZ-treated mice was injected with AAV1-null vectors (same vector capsid but without expression of any transgene).

Animals treated with a combination of AAV1-mhINS+ AAV1-mhGck showed significant reduction in blood glucose levels both in fasted and fed conditions (FIGS. 15 and 16, respectively) compared with AAV1-null vector-treated mice or single treatment with AAV1-mhINS or AAV1-mhGck.

Example 8: Combined Therapy: Gene Therapy with AAV1-mhGck+Exogenous Insulin in T1D and T2D The present invention have also evaluated whether AAV1-mhGck gene therapy per se may have therapeutic benefit for treating diabetes.

a) Evaluation of AAV1-mhGcK in T1D.

To this end, we injected AAV1-mhGcK vectors (10E12 vg/kg) into the hindlimbs of c57b16 diabetic mice. Experimental T1D was induced by STZ administration and viral vectors (AAV1-mhGck) were injected 15 days after STZ. A control group of STZ-treated mice was injected with AAV1-null vectors (same vector capsid but without expression of any transgene). Two-months after AAV injection an insulin tolerance test was performed using low doses of insulin (0,375 U/kg). FIG. 17 shows that AAV1-mhGck treatment dramatically increase glucose uptake and reduce glycemia in the presence of exogenous insulin. These results indicate that gene therapy with AAV1-mhGck could be combined with regular exogenous insulin injections to improve the conventional treatment of T1D diabetes.

b) AAV1-Gck Treatment in T2D.

The inventors performed experiments in high fat fed animals as a model of T2D. In these animals, AAV1-rGck vectors (2E12 vg/kg) were injected in hindlimb muscles before the induction of diabetes by the high fat diet (HFD). Three months after HFD an intraperitoneal insulin tolerance test (0.75 U/kg) was performed. Insulin sensitivity of AAV1-Gck-treated mice was similar to control healthy mice while HFD fed mice were insulin resistant (FIG. 18). These data demonstrate that AAV1-GcK gene therapy per se could be considered as a treatment for diabetic patients in which insulin production is still present, such as early phases of T2D patients.

REFERENCES 1. 1997. Report of the Expert Committee on the Diagnosis and Classification of Diabetes Mellitus. Diabetes Care 20:1183-1197.
2. Eizirik, D. L., and Mandrup-Poulsen, T. 2001. A choice of death—the signal-transduction of immune-mediated beta-cell apoptosis. Diabetologia 44:2115-2133.
3. Mathis, D., Vence, L., and Benoist, C. 2001. beta-Cell death during progression to diabetes. Nature 414:792-798.
4. Kahn, S. E., Hull, R. L., and Utzschneider, K. M. 2006. Mechanisms linking obesity to insulin resistance and type 2 diabetes. Nature 444:840-846.
5. Roglic, G., and Unwin, N. 2009. Mortality attributable to diabetes: estimates for the year 2010. Diabetes Res Clin Pract 87:15-19.

6. 2009. Diabetes Atlas, 4th Edition: International Diabetes Federation.
7. Beran, D., and Yudkin, J. S. 2006. Diabetes care in sub-Saharan Africa. Lancet 368:1689-1695.
8. Gale, E. A. 2006. Dying of diabetes. Lancet 368:1626-1628.
9. Greenwood, H. L., Singer, P. A., Downey, G. P., Martin, D. K., Thorsteinsdottir, H., and Daar, A. S. 2006. Regenerative medicine and the developing world. PLoS Med 3:e381.
10. Heine, R. J., Bilo, H. J., Sikkenk, A. C., and van der Veen, E. A. 1985. Mixing short and intermediate acting insulins in the syringe: effect on postprandial blood glucose concentrations in type I diabetics. Br Med J (Clin Res Ed) 290:204-205.
11. Binder, C., Lauritzen, T., Faber, O., and Pramming, S. 1984. Insulin pharmacokinetics. Diabetes Care 7:188-199.
12. The Diabetes Control and Complications Trial Research Group. The effect of intensive treatment of diabetes on the development and progression of long-term complications in insulin-dependent diabetes mellitus. 1993. N Engl J Med 329:977-986.
13. Cryer, P. E. 2001. Hypoglycemia risk reduction in type 1 diabetes. Exp Clin Endocrinol Diabetes 109 Suppl 2:S412-423.
14. Cryer, P. E. 2002. Hypoglycaemia: the limiting factor in the glycaemic management of Type I and Type II diabetes. Diabetologia 45:937-948.
15. Correa-Giannella, M. L., and Raposo do Amaral, A. S. 2009. Pancreatic islet transplantation. Diabetol Metab Syndr 1:9.
16. Shapiro, A. M., Lakey, J. R., Ryan, E. A., Korbutt, G. S., Toth, E., Warnock, G. L., Kneteman, N. M., and Rajotte, R. V. 2000. Islet transplantation in seven patients with type 1 diabetes mellitus using a glucocorticoid-free immunosuppressive regimen. N Engl J Med 343:230-238.
17. Ryan, E. A., Paty, B. W., Senior, P. A., Bigam, D., Alfadhli, E., Kneteman, N. M., Lakey, J. R., and Shapiro, A. M. 2005. Five-year follow-up after clinical islet transplantation. Diabetes 54:2060-2069.
18. Elliott, R. B., Escobar, L., Tan, P. L., Muzina, M., Zwain, S., and Buchanan, C. 2007. Live encapsulated porcine islets from a type 1 diabetic patient 9.5 yr after xenotransplantation. Xenotransplantation 14:157-161.
19. Hering, B. J., and Walawalkar, N. 2009. Pig-to-nonhuman primate islet xenotransplantation. Transpl Immunol 21:81-86.
20. Trucco, M. 2005. Regeneration of the pancreatic beta cell. J Clin Invest 115:5-12.
21. Dong, H., and Woo, S. L. 2001. Hepatic insulin production for type 1 diabetes. Trends Endocrinol Metab 12:441-446.
22. Lee, H. C., Kim, S. J., Kim, K. S., Shin, H. C., and Yoon, J. W. 2000. Remission in models of type 1 diabetes by gene therapy using a single-chain insulin analogue. Nature 408:483-488.
23. Cheung, A. T., Dayanandan, B., Lewis, J. T., Korbutt, G. S., Rajotte, R. V., Bryer-Ash, M., Boylan, M. O., Wolfe, M. M., and Kieffer, T. J. 2000. Glucose-dependent insulin release from genetically engineered K cells. Science 290:1959-1962.
24. Ferber, S., Halkin, A., Cohen, H., Ber, I., Einav, Y., Goldberg, I., Barshack, I., Seijffers, R., Kopolovic, J., Kaiser, N., et al. 2000. Pancreatic and duodenal homeobox gene 1 induces expression of insulin genes in liver and ameliorates streptozotocin-induced hyperglycemia. Nat Med 6:568-572.
25. Kojima, H., Fujimiya, M., Matsumura, K., Younan, P., Imaeda, H., Maeda, M., and Chan, L. 2003. NeuroD-betacellulin gene therapy induces islet neogenesis in the liver and reverses diabetes in mice. Nat Med 9:596-603. Epub 2003 Apr. 2021.
26. Kahn, B. B. 1996. Lilly lecture 1995. Glucose transport: pivotal step in insulin action. Diabetes 45:1644-1654.
27. Printz, R. L., Magnuson, M. A., and Granner, D. K. 1993. Mammalian glucokinase. Annu Rev Nutr 13:463-496.
28. Postic, C., Leturque, A., Printz, R. L., Maulard, P., Loizeau, M., Granner, D. K., and Girard, J. 1994. Development and regulation of glucose transporter and hexokinase expression in rat. Am J Physiol 266:E548-559.
29. Printz, R. L., Koch, S., Potter, L. R., O'Doherty, R. M., Tiesinga, J. J., Moritz, S., and Granner, D. K. 1993. Hexokinase II mRNA and gene structure, regulation by insulin, and evolution. J Biol Chem 268:5209-5219.
30. Riu, E., Mas, A., Ferre, T., Pujol, A., Gros, L., Otaegui, P., Montoliu, L., and Bosch, F. 2002. Counteraction of type 1 diabetic alterations by engineering skeletal muscle to produce insulin: insights from transgenic mice. Diabetes 51:704-711.
31. White, M. F., and Kahn, C. R. 1994. The insulin signaling system. J Biol Chem 269:1-4.
32. Otaegui, P. J., Ferre, T., Pujol, A., Riu, E., Jimenez, R., and Bosch, F. 2000. Expression of glucokinase in skeletal muscle: a new approach to counteract diabetic hyperglycemia. Hum Gene Ther 11:1543-1552.
33. Matschinsky, F. M. 1996. Banting Lecture 1995. A lesson in metabolic regulation inspired by the glucokinase glucose sensor paradigm. Diabetes 45:223-241.
34. Jimenez-Chillaron, J. C., Newgard, C. B., and Gomez-Foix, A. M. 1999. Increased glucose disposal induced by adenovirus-mediated transfer of glucokinase to skeletal muscle in vivo. Faseb J 13:2153-2160.
35. Otaegui, P. J., Ontiveros, M., Ferre, T., Riu, E., Jimenez, R., and Bosch, F. 2002. Glucose-regulated glucose uptake by transplanted muscle cells expressing glucokinase counteracts diabetic hyperglycemia. Hum Gene Ther 13:2125-2133.
36. Mas, A., Montane, J., Anguela, X. M., Munoz, S., Douar, A. M., Riu, E., Otaegui, P., and Bosch, F. 2006. Reversal of type 1 diabetes by engineering a glucose sensor in skeletal muscle. Diabetes 55:1546-1553.
37. Daya S & Berns K I. 2008. Gene therapy using adeno-associated virus vectors. Clin Microbiol Rev 21(4):583-593.
38. Brantly M L, Chulay J D, Wang L, Mueller C, Humphries M, Spencer L T, Rouhani F, Conlon T J, Calcedo R, Betts M R, Spencer C, Byrne B J, Wilson J M, Flotte T R. 2009. Sustained transgene expression despite T lymphocyte responses in a clinical trial of rAAV1-AAT gene therapy Proc Natl Acad Sci USA 106(38):16363-16368.
39. Kaplitt M G, Feigin A, Tang C, Fitzsimons H L, Mattis P, Lawlor P A, Bland R J, Young D, Strybing K, Eidelberg D, During M J. 2007. Safety and tolerability of gene therapy with an adeno-associated virus (AAV) borne GAD gene for Parkinson's disease: an open label, phase I trial. Lancet 369(9579):2097-2105.

40. Maguire A M, High K A, Auricchio A, Wright J F, Pierce E A, Testa F, Mingozzi F, Bennicelli J L, Ying G S, Rossi S, Fulton A, Marshall K A, Banfi S, Chung D C, Morgan J I, Hauck B, Zelenaia O, Zhu X, Raffini L, Coppieters F, De Baere E, Shindler K S, Volpe N J, Surace E M, Acerra C, Lyubarsky A, Redmond T M, Stone E, Sun J, McDonnell J W, Leroy B P, Simonelli F, Bennett J. 2009. Age-dependent effects of RPE65 gene therapy for Leber's congenital amaurosis: a phase 1 dose-escalation trial. Lancet 374(9701):1597-1605.

41. Maguire A M, Simonelli F, Pierce E A, Pugh E N Jr, Mingozzi F, Bennicelli J, Banfi S, Marshall K A, Testa F, Surace E M, Rossi S, Lyubarsky A, Arruda V R, Konkle B, Stone E, Sun J, Jacobs J, Dell'Osso L, Hertle R, Ma J X, Redmond T M, Zhu X, Hauck B, Zelenaia O, Shindler K S, Maguire M G, Wright J F, Volpe N J, McDonnell J W, Auricchio A, High K A, Bennett J. 2008. Safety and efficacy of gene transfer for Leber's congenital amaurosis. N Engl J Med 358(21):2240-2248.

42. Manno C S, Pierce G F, Arruda V R, Glader B, Ragni M, Rasko J J, Ozelo M C, Hoots K, Blatt P, Konkle B, Dake M, Kaye R, Razavi M, Zajko A, Zehnder J, Rustagi P K, Nakai H, Chew A, Leonard D, Wright J F, Lessard R R, Sommer J M, Tigges M, Sabatino D, Luk A, Jiang H, Mingozzi F, Couto L, Ertl H C, High K A, Kay M A. 2006. Successful transduction of liver in hemophilia by AAV-Factor IX and limitations imposed by the host immune response. Nat Med 12(3):342-347.

43. Mendell J R, Rodino-Klapac L R, Rosales-Quintero X, Kota 5, Coley B D, Galloway G, Craenen J M, Lewis S, Malik V, Shilling C, Byrne B J, Conlon T, Campbell K J, Bremer W G, Viollet L, Walker C M, Sahenk Z, Clark K R. 2009. Limb-girdle muscular dystrophy type 2D gene therapy restores alpha-sarcoglycan and associated proteins. Ann Neurol 66(3):290-297.

44. Stroes E S, Nierman M C, Meulenberg J J, Franssen R, Twisk J, Henny C P, Maas M M, Zwinderman A H, Ross C, Aronica E, High K A, Levi M M, Hayden M R, Kastelein J J, Kuivenhoven J A. 2008. Intramuscular administration of AAV1-lipoprotein lipase S447X lowers triglycerides in lipoprotein lipase-deficient patients. Arterioscler Thromb Vasc Biol 28(12):2303-2304.

45. Jiang H, Pierce G F, Ozelo M C, de Paula E V, Vargas J A, Smith P, Sommer J, Luk A, Manno C S, High K A, Arruda V R. 2006. Evidence of multiyear factor IX expression by AAV-mediated gene transfer to skeletal muscle in an individual with severe hemophilia B. Mol Ther 14(3):452-455.

46. Niemeyer G P, Herzog R W, Mount J, Arruda V R, Tillson D M, Hathcock J, van Ginkel F W, High K A, Lothrop C D Jr. 2009. Long-term correction of inhibitor-prone hemophilia B dogs treated with liver-directed AAV2-mediated factor IX gene therapy. Blood 113(4):797-806.

47. Simonelli F, Maguire A M, Testa F, Pierce E A, Mingozzi F, Bennicelli J L, Rossi S, Marshall K, Banfi S, Surace E M, Sun J, Redmond T M, Zhu X, Shindler K S, Ying G S, Ziviello C, Acerra C, Wright S F, McDonnell S W, High K A, Bennett J, Auricchio A. 2010. Gene therapy for Leber's congenital amaurosis is safe and effective through 1.5 years after vector administration. Mol Ther 18(3):643-650.

48. Sharp, P. M. and Li, W. H. 1987. The codon Adaptation Index—a measure of directional synonymous codon usage bias, and its potential applications. Nucleic Acids Res. 15 (3).

49. Ayuso E, Mingozzi F, Montane J, Leon X, Anguela X M, Haurigot V, Edmonson S A, Africa L, Zhou S, High K A, Bosch F, Wright J F. 2010. High AAV vector purity results in serotype- and tissue-independent enhancement of transduction efficiency. Gene Ther. 17(4):503-10.

50. Anderson H R, Stitt A W, Gardiner T A, Lloyd S J, Archer D B. 1993 Induction of alloxan/streptozotocin diabetes in dogs: a revised experimental technique. Lab Anim. July; 27(3):281-5.

The invention claimed is:

1. A method of treatment of diabetes in a subject which comprises administering to the subject a therapeutically effective amount of a gene therapy composition which comprises a single vector carrying and allowing the expression of both an insulin gene (Ins) and a glucokinase gene (Gck) operatively linked, wherein the coding sequence of the insulin gene and the coding sequence of the glucokinase gene are mutated with the purpose of increasing protein production in said subject and in such a way that the codon adaptation index of these mutated coding sequences is higher than 0.9 and wherein the gene therapy composition is administered in a single dose avoiding repeated periodical administration.

2. The method according to claim 1 wherein the single dose is administered to muscle tissue by means of a single multi-needle injection.

3. The method according to claim 1, wherein the vector is an adeno-associated virus (AAV) based vector.

4. The method according to claim 3, wherein the vector is an adeno-associated virus vector of serotype 1 (AAV1).

5. The method according to claim 1, wherein the subject is a dog or human.

6. The method according to claim 4, wherein the subject is a human.

7. The method of claim 1, whereby fasting plasma glucose levels in the subject are normalized for at least two years following administration of the single dose.

8. A method according to claim 1 wherein the insulin gene encodes for human insulin and the glucokinase gene encodes for human glucokinase.

9. A method of treatment of diabetes which comprises administering to a human or dog in need of such treatment a therapeutically effective amount of a gene therapy composition which comprises a single adeno-associated virus vector of serotype 1 (AAV1) carrying and allowing the expression of both an insulin gene (Ins) and a glucokinase gene (Gck) operatively linked, wherein the coding sequence of the insulin gene and the coding sequence of the glucokinase gene are mutated with the purpose of increasing protein production in said human or dog and in such a way that the codon adaptation index of these mutated coding sequences is higher than 0.9 and wherein the gene therapy composition is administered in a single dose avoiding repeated periodical administration.

10. The method of claim 9, whereby fasting plasma glucose levels in the human or dog are normalized for at least two years following administration of the single dose.

11. A method according to claim 9 wherein the insulin gene encodes for human insulin and the glucokinase gene encodes for human glucokinase.

* * * * *